(12) United States Patent
Cavanaugh, II et al.

(10) Patent No.: US 12,156,788 B2
(45) Date of Patent: Dec. 3, 2024

(54) DRESSING WITH EPITHELIALIZATION AND SCAR REDUCTION FEATURE

(71) Applicant: KCI Licensing, Inc., San Antonio, TX (US)

(72) Inventors: Matthew Francis Cavanaugh, II, San Antonio, TX (US); Prathamesh Madhav Kharkar, San Antonio, TX (US)

(73) Assignee: KCI Licensing Inc., San Antonio, TX (US)

( * ) Notice: Subject to any disclaimer, the term of this patent is extended or adjusted under 35 U.S.C. 154(b) by 53 days.

(21) Appl. No.: 17/629,721

(22) PCT Filed: Jul. 29, 2020

(86) PCT No.: PCT/IB2020/057151
§ 371 (c)(1),
(2) Date: Jan. 24, 2022

(87) PCT Pub. No.: WO2021/019461
PCT Pub. Date: Feb. 4, 2021

(65) Prior Publication Data
US 2022/0296770 A1 Sep. 22, 2022

Related U.S. Application Data

(60) Provisional application No. 62/881,555, filed on Aug. 1, 2019.

(51) Int. Cl.
*A61F 13/05* (2024.01)
*A61F 13/0246* (2024.01)
(Continued)

(52) U.S. Cl.
CPC ............ *A61F 13/05* (2024.01); *A61F 13/025* (2013.01); *A61L 15/225* (2013.01); *A61L 15/425* (2013.01); *A61L 15/585* (2013.01); *A61M 1/915* (2021.05)

(58) Field of Classification Search
CPC ............ A61F 13/00068; A61F 13/0216; A61F 13/025; A61F 13/0246; A61M 1/915
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion for corresponding Application No. PCT/IB2020/057151 mailed Oct. 7, 2020.
(Continued)

*Primary Examiner* — Philip R Wiest
*Assistant Examiner* — Matthew Wrubleski

(57) ABSTRACT

Provided are systems, dressings, and methods suitable for treating a tissue site, such as an incision or linear wound, for example. The systems, dressings, and methods relate to a dressing assembly that may include a dressing bolster, a comfort layer, and a polymeric enhancement layer. The dressing bolster may include foam and may have a first side and a second side. A first side of the comfort layer may be coupled to the second side of the dressing bolster, and a first side of the polymeric enhancement layer may be coupled to the second side of the comfort layer. An opposing second
(Continued)

side of the polymeric enhancement layer may be configured to directly contact the tissue site. Other systems, dressings, apparatuses, and methods are disclosed.

23 Claims, 13 Drawing Sheets

(51) Int. Cl.
*A61L 15/22* (2006.01)
*A61L 15/42* (2006.01)
*A61L 15/58* (2006.01)
*A61M 1/00* (2006.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0227969 A1* | 9/2009 | Jaeb ............... A61M 1/74 604/313 |
| 2011/0230849 A1* | 9/2011 | Coulthard ........... A61M 1/962 604/319 |
| 2015/0313762 A1* | 11/2015 | Simmons .......... A61F 13/0246 604/543 |
| 2018/0250170 A1* | 9/2018 | Øelund ................. B32B 7/06 |
| 2018/0035333 A1 | 12/2018 | Locke et al. |
| 2019/0274889 A1* | 9/2019 | Steward ......... A61F 13/00068 |
| 2020/0008981 A1* | 1/2020 | Wheldrake ..... A61F 13/00017 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |

(56) References Cited

FOREIGN PATENT DOCUMENTS

| | | |
|---|---|---|
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2012112204 A1 | 8/2012 |
| WO | 2017040045 A1 | 3/2017 |
| WO | 2018227144 A1 | 12/2018 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

DRESSING WITH EPITHELIALIZATION AND SCAR REDUCTION FEATURE

CROSS-REFERENCE TO RELATED APPLICATIONS

This application claims the benefit of priority to U.S. Provisional Application No. 62/881,555, filed on Aug. 1, 2019, which is incorporated herein by reference in its entirety.

TECHNICAL FIELD

This disclosure relates generally to medical treatment systems and, more particularly, but not by way of limitation, to absorbent dressings, systems, and methods for treating a tissue site with reduced pressure.

BACKGROUND

Clinical studies and practice have shown that reducing pressure in proximity to a tissue site can augment and accelerate growth of new tissue at the tissue site. The applications of this phenomenon are numerous, but have proven particularly advantageous for treating wounds. Regardless of the etiology of a wound, whether trauma, surgery, or another cause, proper care of a wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

SUMMARY

Shortcomings with certain aspects of tissue treatment dressings, systems, and methods are addressed as shown and described in a variety of illustrative, non-limiting example embodiments herein.

In some example embodiments, a system for treating a tissue site may include a dressing assembly and a reduced-pressure source. The dressing assembly may include a dressing bolster, a comfort layer, a first sealing member, a second sealing member, a gasket member, and polymeric enhancement layer. The dressing bolster may have a first side and an opposing second side. The comfort layer may have a first side and an opposing second side. The first side of the comfort layer may be coupled to the second side of the dressing bolster. The first sealing member may cover the first side of the dressing bolster. The second sealing member may be positioned on and extend outward from the second side of the dressing bolster and be coupled to a portion of the first sealing member. The gasket member may be positioned on the second side of the dressing bolster. The polymeric enhancement layer may have a first side and an opposing second side. The first side of the polymeric enhancement layer may be coupled to the second side of the comfort layer. The second side of the polymeric enhancement layer may be configured to directly contact the tissue site. The reduced-pressure source may be configured to be coupled in fluid communication with the dressing assembly.

In some example embodiments, a system for treating a tissue site may include a dressing assembly, a sealing member, and a reduced-pressure source. The dressing assembly may include a dressing bolster, a comfort layer, and a polymeric enhancement layer. The dressing bolster have a first side and a second side. The comfort layer may have a first side and a second side. The first side of the comfort layer may be coupled to the second side of the dressing bolster. The polymeric enhancement layer may have a first side and an opposing second side. The first side of the polymeric enhancement layer may be coupled to the second side of the comfort layer. The second side of the polymeric enhancement layer may be configured to directly contact the tissue site. The sealing member may be configured to cover the dressing assembly and to create a sealed space between the dressing assembly and the tissue site. The reduced-pressure source may be configured to be coupled in fluid communication with the sealed space.

In some example embodiments, a dressing assembly may include a dressing bolster, a comfort layer, and a polymeric enhancement layer. The dressing bolster may include foam and may have a first side and a second side. The comfort layer may have a first side and a second side. The first side of the comfort layer may be coupled to the second side of the dressing bolster. The polymeric enhancement layer may have a first side and an opposing second side. The first side of the polymeric enhancement layer may be coupled to the second side of the comfort layer. The second side of the polymeric enhancement layer may be configured to directly contact the tissue site.

In some example embodiments, a method for treating a tissue site may include disposing a dressing assembly proximate to the tissue site. The dressing assembly may include a dressing bolster, a comfort layer coupled to the dressing bolster, and a polymeric enhancement layer coupled to the comfort layer. Further, the method may include covering the dressing assembly with a sealing member to form a sealed space between the dressing assembly and the tissue site. Further, the method may include extracting fluid from the tissue site into the dressing assembly. Further, the method may include exposing the tissue site to a silicone material or an acrylic material or both a silicone material and an acrylic material associated with the polymeric enhancement layer.

In some example embodiments, a system for treating a tissue site may include a dressing assembly. The dressing assembly may be configured to be coupled to a reduced pressure source and may include a dressing bolster, a comfort layer, a sealing member, and a polymeric layer. The dressing bolster may have a first side and an opposing second side. The comfort layer may have a first side and an opposing second side. The first side of the comfort layer may be positioned on the second side of the dressing bolster. The sealing member may be configured to cover the first side of the dressing bolster. The polymeric layer may include silicone and may have a first side and an opposing second side. The first side of the polymeric layer may be coupled to the second side of the comfort layer. The second side of the polymeric layer may be configured to directly contact the tissue site. Further, the polymeric layer may include a plurality of apertures disposed through the polymeric layer between the first side and the second side of the polymeric layer.

In further examples, the polymeric layer may be substantially aligned along a longitudinal axis of the dressing assembly and configured to be positioned along a length of an incision at the tissue site. In further examples, the plurality of apertures through the polymeric layer may be substantially aligned along a longitudinal axis of the dressing assembly and configured to be positioned along a length of an incision at the tissue site. At least one of the plurality of apertures may include a diameter between about 2 millimeters to about 10 millimeters.

In further examples, the plurality of apertures through the polymeric layer may be positioned in at least one longitudinal row along the longitudinal axis of the dressing assembly. In further examples, the at least one longitudinal row of apertures may include a first longitudinal row of apertures and a second longitudinal row of apertures, and the first longitudinal row of apertures may be offset from the second longitudinal row of apertures.

In further examples, the second side of the comfort layer may have a first area and the second side of the polymeric layer may have a second area, and the first area may be larger than the second area. In further examples, the second area may be less than 30 percent of the first area. In further examples, at least a portion of the first area of the comfort layer and the second area of the polymeric layer are both configured to directly contact the tissue site.

Other features and advantages of the illustrative example embodiments will become apparent with reference to the drawings and detailed description that follow.

DETAILED DESCRIPTION OF EXAMPLE EMBODIMENTS

The following description of example embodiments enables a person skilled in the art to make and use the subject matter set forth in the appended claims. Certain details already known in the art may be omitted. Further, the following detailed description is illustrative and non-limiting.

Figure 1:
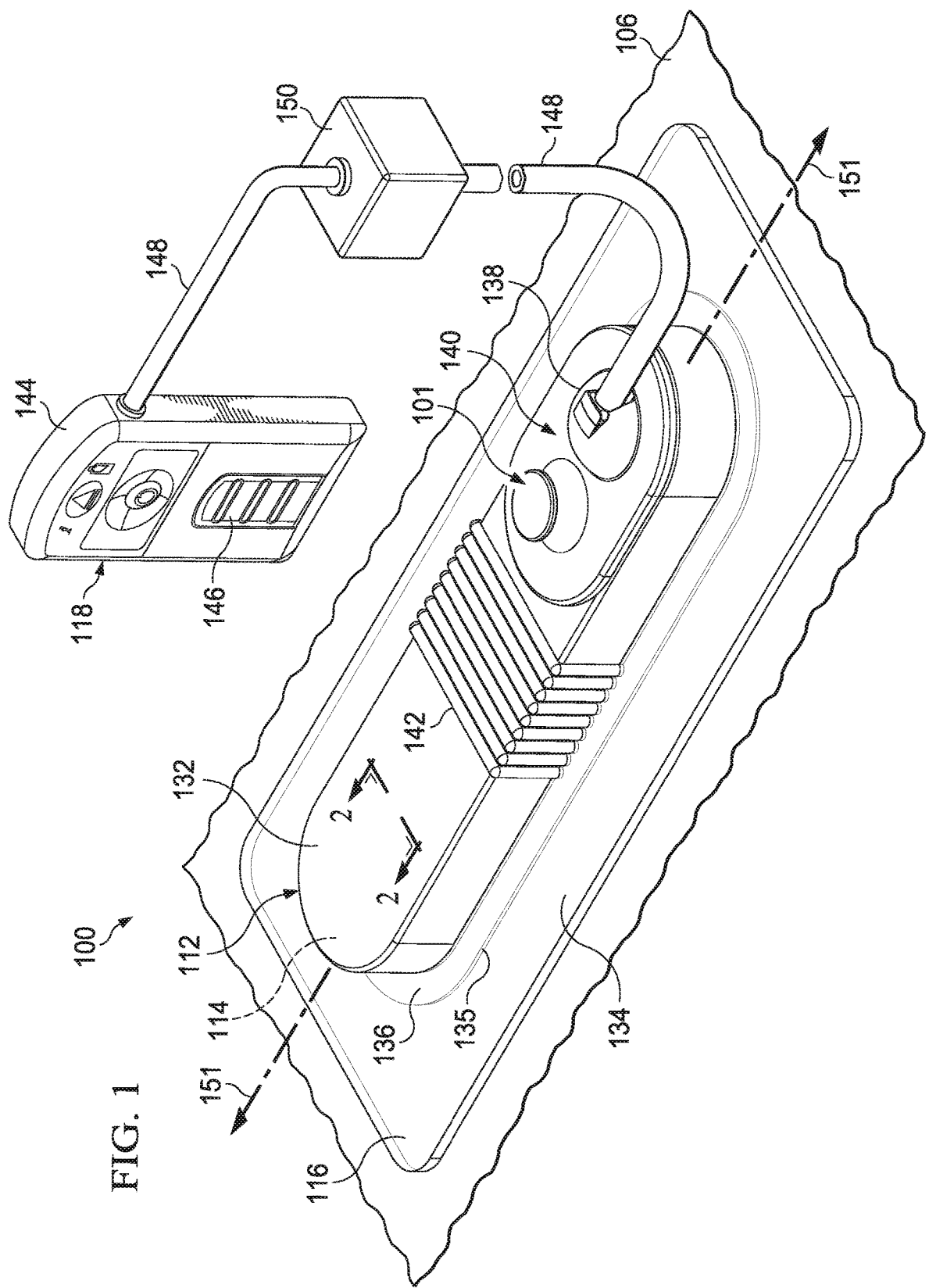
FIG. 1 is a perspective view of an illustrative example embodiment of a system for treating a tissue site.
Figure 2:
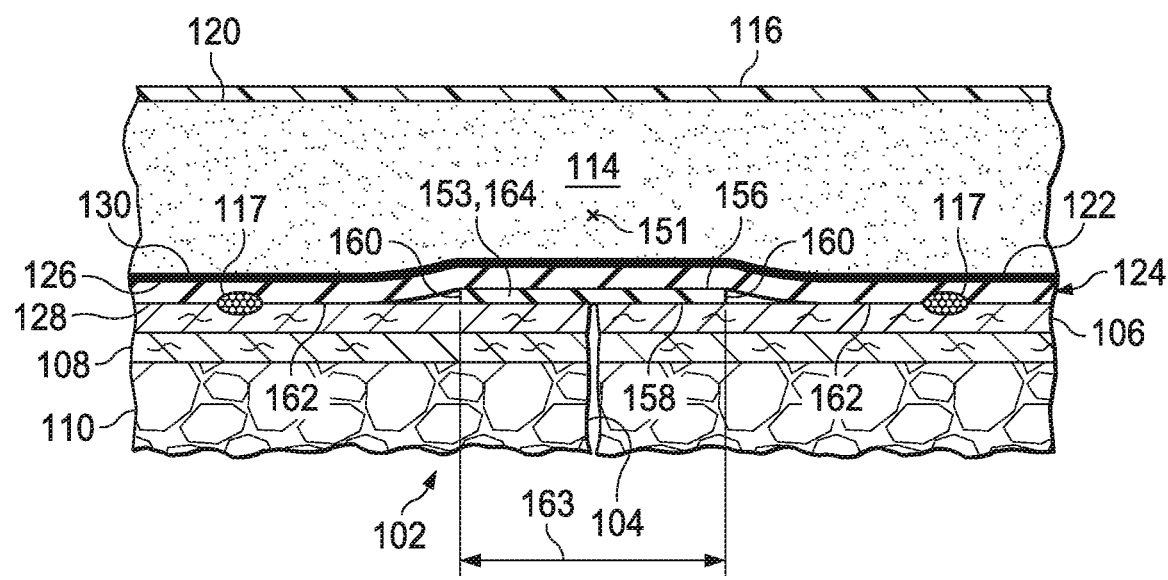
FIG. 2 is a cross-section of a portion of an illustrative example embodiment of a dressing assembly depicted in FIG. 1, taken along line 2-2.

Referring primarily to FIGS. 1 and 2, presented is an illustrative, non-limiting example embodiment of a treatment system 100 for treating a tissue site 102, such as an incision 104. The incision 104 is shown extending through or involving epidermis 106, dermis 108, and subcutaneous tissue 110. The treatment system 100 may also be used with other tissue sites, and may be utilized with or without reduced pressure as described herein.

In some embodiments, the treatment system 100 may include a dressing assembly 112 having a dressing bolster 114, which may be referred to as a manifold member 114. In addition, some embodiments of the treatment system 100 may include a sealing member 116 and a reduced-pressure subsystem 118. Some embodiments of the treatment system 100 may also include a reduced-pressure indicator 101. While the treatment system 100 is shown in the context of a reduced-pressure dressing over an incision 104, the treatment system 100 may be used on other tissue sites, including open wounds. Further, features may be optionally added to or omitted from the treatment system 100 to suit different therapeutic applications, scenarios, or preferences, and thus, features described herein are not to be considered essential unless explicitly stated.

In some embodiments, the dressing bolster 114 may include a first side 120 and a second side 122 positioned opposite or facing opposite to the first side 120. The first side 120 of the dressing bolster 114 may be configured to face outward from or away from the tissue site 102, and the second side 122 of the dressing bolster 114 may be configured to face inward or toward the tissue site 102. The second side 122 of the dressing bolster 114 may also be referred to as a second, inward-facing side 122.

The dressing bolster 114 may be formed from any bolster material or manifold material that provides a vacuum space, or treatment space. Reduced pressure applied to the dressing bolster 114 may enhance the permeability of the dressing bolster 114. For example, the dressing bolster 114 may be formed from a porous and permeable foam or foam-like material, a member formed with pathways, a graft, a gauze, or any combination thereof. In some embodiments, the dressing bolster 114 may be a reticulated, open-cell polyurethane or polyether foam that may be fluid permeable. One example of a suitable foam material may be a GRANUFOAM™ material available from Kinetic Concepts, Inc. (KCI) of San Antonio, Texas.

The term "manifold" as used herein may refer to a substance or structure that may assist in applying reduced pressure to, delivering fluids to, or removing fluids from a tissue site. A manifold may include a plurality of flow channels or pathways. The plurality of flow channels may be interconnected to improve distribution of fluids provided to and removed from an area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

The reticulated pores of the GRANUFOAM™ material may be helpful in carrying out the manifold function, but as stated above, other materials may be utilized. A material with a higher or lower density than the GRANUFOAM™ material may be desirable in some embodiments. This material may have, for example, a smaller pore size than the GRANUFOAM™ material. Among the many possible materials, the following may be used without limitation: GRANUFOAM™ material, FXI technical foam, gauze, a flexible channel-containing member, a graft, and other similar materials. In some embodiments, ionic silver may be added to the material, such as, for example, by a micro bonding process. Other substances, such as antimicrobial agents, may also be added to the material.

In some embodiments, a comfort layer 124 may be coupled, for example, by a heat bond 130 or other suitable technique to the second, inward-facing side 122 of the dressing bolster 114. The comfort layer 124 may include a first side 126 and a second side 128 positioned opposite or facing opposite to the first side 126. The first side 126 of the comfort layer 124 may be configured to face outward from or away from the tissue site 102, and the second side 128 of the comfort layer 124 may be configured to face inward or toward the tissue site 102. The first side 126 of the comfort layer 124 may be coupled to the second side 122 of the dressing bolster 114. Herein, the comfort layer 124 may also be referred to as an interfacial layer, a tissue interface layer, or tissue contact layer. Further, the second side 128 of the comfort layer 124 may also be referred to as a second, inward-facing side 128.

The comfort layer 124 may enhance patient comfort when the dressing bolster 114 is adjacent to or in contact with the epidermis 106 of a patient. The comfort layer 124 may be any material that helps prevent skin irritation and discomfort while allowing fluid transmission through the comfort layer 124. As non-limiting examples, the comfort layer 124 may include or be formed of a woven material, an elastic material, a polyester knit textile substrate, a non-woven material, or a fenestrated film. As another non-limiting example, an INTERDRY™ textile material available from Milliken Chemical, a division of Milliken & Company, Inc. of Spartanburg, South Carolina, may be utilized. In some embodiments, the comfort layer 124 may include antimicrobial substances, such as silver.

Figure 4:
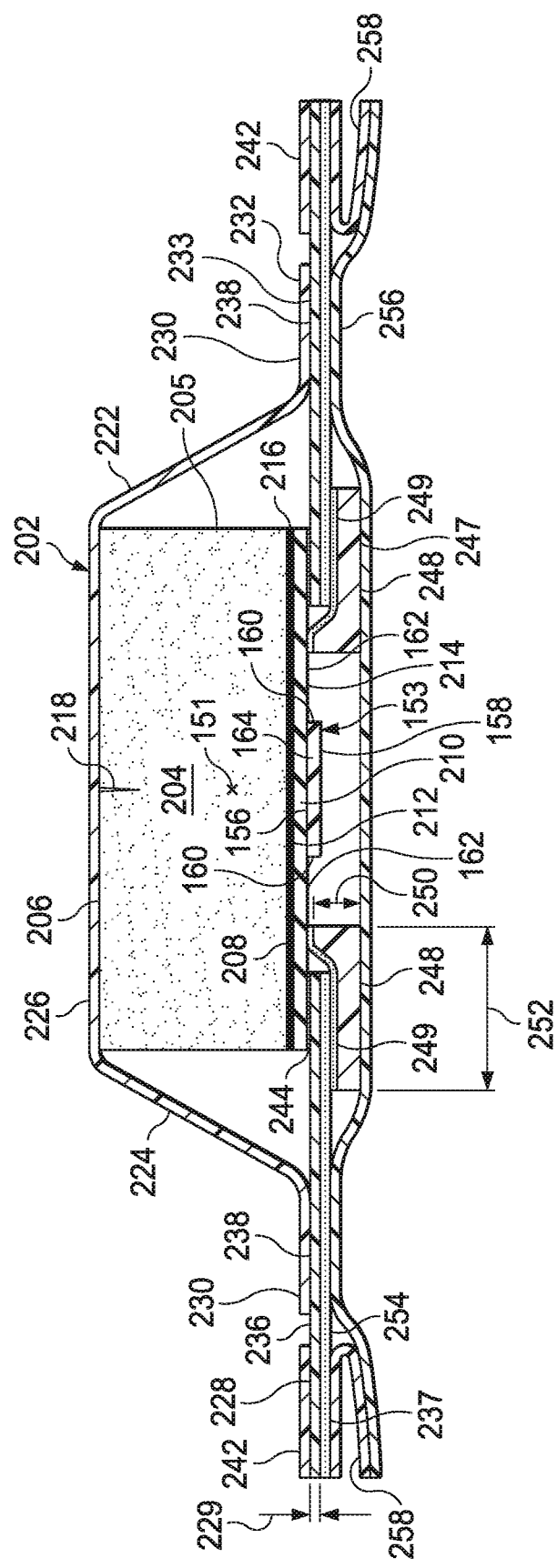
FIG. 4 is a cross-section of an illustrative example embodiment of a dressing assembly depicted in FIG. 3, taken along line 4-4.

In some embodiments, the dressing bolster 114 may include a plurality of flexibility notches or recesses, analogous to notches 218 shown in FIG. 4, for example, that may be lateral cuts in the dressing bolster 114 on the first side 120. The dressing bolster 114 may additionally or alternatively include one or more longitudinal cuts or notches, which may intersect the lateral cuts or notches. The flexibility notches may enhance the flexibility of the dressing bolster 114. The enhanced flexibility may be particularly useful when the dressing assembly 112 is applied over a joint or other area of movement on a patient. The flexibility notches may also take various shapes without limitation, such as, for example, hexagons, slits, or squares.

In some embodiments, the dressing bolster 114 may include lateral edges (not shown) that are orthogonal relative to the second, inward-facing side 122 of the dressing bolster 114. The lateral edges of the dressing bolster 114 may be analogous to lateral edges 205 of dressing bolster 204 depicted in FIG. 4. The lateral edges of the dressing bolster 114 may also have a beveled edge or angled edge. The angled or beveled edge may help distribute shear stress between the dressing bolster 114 and the epidermis 106 of a patient. The lateral edges of the dressing bolster 114 may substantially correspond to lateral edges (not shown) of the comfort layer 124.

The sealing member 116 may provide a fluid seal over the dressing bolster 114 and a portion of the epidermis 106 of the patient. As such, the sealing member 116 may be formed from any material that allows for a fluid seal. Herein, the terms "fluid seal," or "seal," may be a seal adequate to maintain reduced pressure at a desired site given the particular reduced-pressure source or subsystem involved. The sealing member 116 may be sealed against the epidermis 106, or against a gasket or drape, by a sealing apparatus, such as, for example, a pressure-sensitive adhesive.

The sealing apparatus may take numerous forms, such as an adhesive sealing tape, drape tape, or strip; double-sided drape tape; pressure-sensitive adhesive; paste; hydrocolloid; hydrogel; or other suitable sealing device. If a tape is used, the tape may be formed of the same material as the sealing member 116 with a pre-applied, pressure-sensitive adhesive. The pressure-sensitive adhesive may be applied on a side of the sealing member 116 adapted to face the epidermis 106, such as an inward-facing side of the sealing member 116. The pressure-sensitive adhesive may provide a fluid seal between the sealing member 116 and the epidermis, and may be utilized in combination with a gasket or drape against the epidermis 106. Before the sealing member 116 is secured to the epidermis 106, removable strips or release liners that cover the pressure-sensitive adhesive may be removed.

In some embodiments, the sealing member 116 may be an elastomeric material configured to provide a fluid seal. "Elastomeric" may refer to a material having the properties of an elastomer, such as a polymeric material that has rubber-like properties. Some elastomers may have ultimate elongations greater than 100% and a significant amount of resilience. The resilience of a material may refer to the ability of the material to recover from an elastic deformation. Examples of elastomers may include, without limitation, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further, sealing member materials may include a silicone drape, a TEGADERM™ drape available from 3M, an acrylic drape, such as one available from Avery Dennison, or an incise drape.

In some embodiments, the sealing member 116 may be comprised of a material including a high moisture vapor transmission rate (MVTR). The use of a high MVTR material for the sealing member 116 may permit moisture vapor to pass through the sealing member 116, external to the dressing assembly 112, while maintaining the fluid seal described herein.

In some embodiments, the sealing member 116 may include a first sealing member portion 132 and a second sealing member portion 134. The first sealing member portion 132 may extend over or cover the first side 120 of the dressing bolster 114. The sealing member 116 may extend further to form a sealing member flange, or sealing member extension 136, which has a first side (not shown) and a second, inward-facing side (not shown). The second, inward-facing side of the sealing member extension 136 may be adapted to face the epidermis 106. An aperture (not shown) may be formed on a portion of the sealing member 116 to allow fluid communication with a conduit interface 138, which may be part of a reduced-pressure assembly 140.

Figure 3:
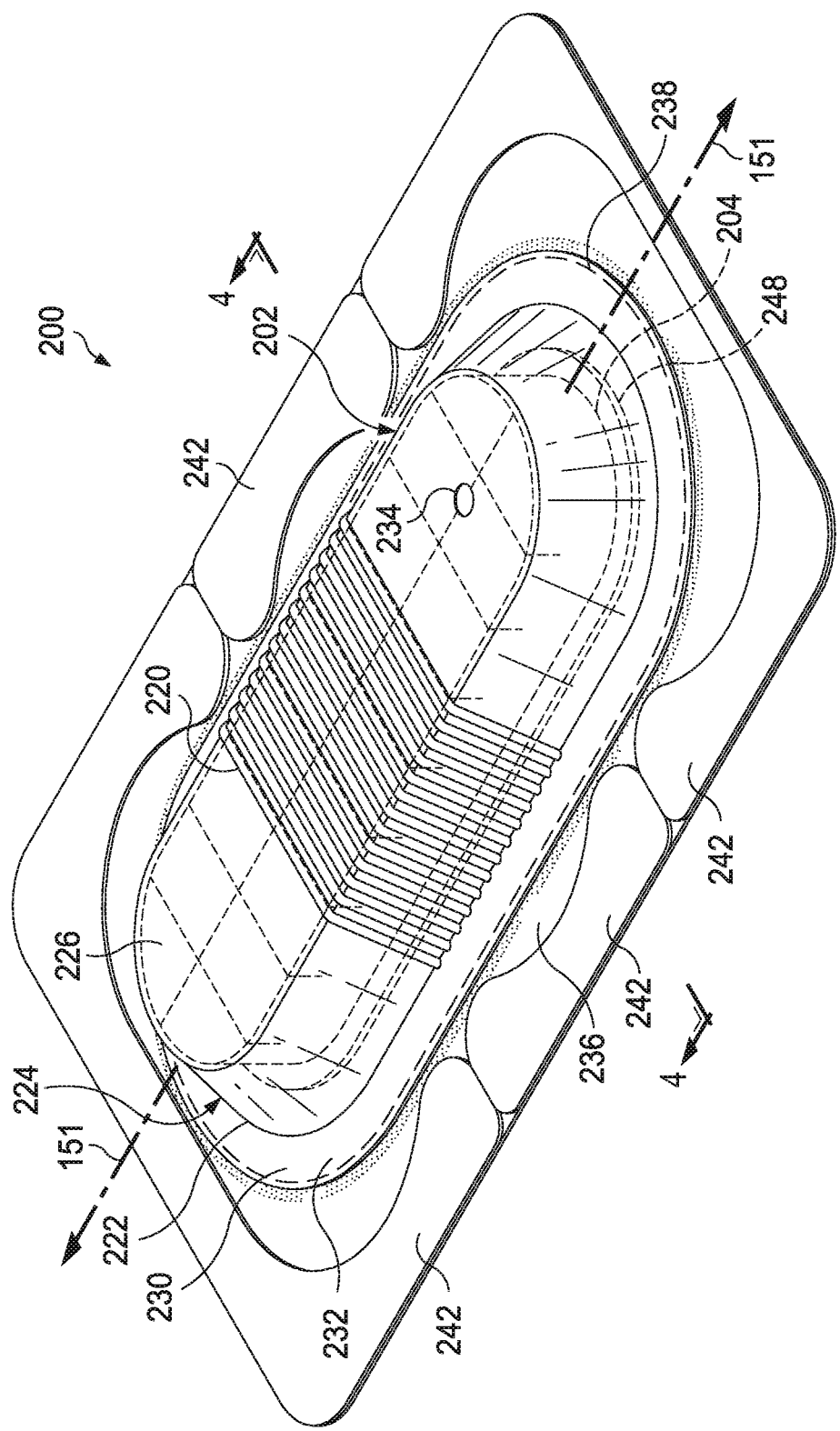
FIG. 3 is a perspective view of an illustrative example embodiment of a portion of a treatment system for treating a tissue site.

The aperture on the sealing member 116 may be analogous to aperture 234 depicted in FIG. 3.

The second, inward-facing side of the sealing member extension 136 may be placed on a first side (not shown) of the second sealing member portion 134, and coupled, such as by an adhesive, a bond 135, a weld (e.g., ultrasonic or RF welding), or by cements. The first side of the second sealing member portion 134 may face away or outward from the epidermis 106. In some example embodiments, the second sealing member 134 may be positioned on and extend outward from the second side 122 of the dressing bolster 114 and be coupled to a portion of the first sealing member 132 as described. Further, in some examples, the first sealing member portion 132 and the second sealing member portion 134 may be integrally formed with one another. Further, the first sealing member portion 132 may include a plurality of bellows 142, folds, or stretch zones. The bellows 142 may provide additional drape material when needed to respond to stretching or other movement. For example, if the dressing assembly 112 is used on a joint, when the joint is flexed, the bellows 142 may provide additional drape material to facilitate such movement.

Prior to application, one or more release members (not shown) may be releasably coupled to the first side of the second sealing member portion 134. The release members may be analogous to release members 242 depicted in FIG. 5, and may provide stiffness to assist with, for example, deployment of the dressing assembly 112. The release members may be, for example, casting paper or a film held on the first side of the second sealing member portion 134. Each release member may have a release agent disposed on a side of the release member configured to contact a component of the dressing assembly 112, such as the second sealing member portion 134, or other components described herein. In some embodiments, the release agent may be a silicone coating and may have a release factor between about 5 grams per centimeter to about 15 grams per centimeter. In some embodiments, the release factor may be between about 2 grams per centimeter to about 6 grams per centimeter. The release agent may facilitate removal of the release member by hand and without damaging or deforming the dressing assembly 112.

Release members suitable for use with the embodiments described herein may be, for example and without limitation, polyester release members specified as FRA 301 (T-36) and FRA 396-T13, available from Fox River Associates, LLC of Geneva, Illinois. The polyester release members may be a polyethylene terephthalate (PET) release member as described herein. In some embodiments, the release members may have a film thickness between about 30 microns to about 70 microns. In some embodiments, the film thickness may be between about 47 microns to about 53 microns. Further, the release members may have a tensile break strength in a machine direction between about 9 kilograms per square millimeter to about 15 kilograms per square millimeter. In a transverse direction, or direction transverse to the machine direction, the release members may have a tensile break strength between about 15 kilograms per square millimeter to about 23 kilograms per square millimeter. The elongation at break of the release members in both the machine direction and the transverse direction may be between about 40 percent to about 140 percent. The release members may have a shrinkage in the machine direction between about 0.0 percent to about 2.5 percent, and a shrinkage in the transverse direction between about 0.0 percent to about 1.2 percent.

The reduced-pressure subsystem 118 may include a reduced-pressure source 144. In some example embodiments, the reduced-pressure source 144 may provide reduced pressure as a part of the treatment system 100. Further, in some examples, the reduced-pressure source 144 may be configured to be coupled in fluid communication with the dressing assembly 112. For example, the reduced-pressure source 144 may be fluidly coupled to the conduit interface 138 by a delivery conduit 148.

As used herein, the term "reduced pressure" may refer to a pressure less than the ambient pressure at a tissue site being subjected to treatment, such as the tissue site 102. The reduced pressure may be less than the atmospheric pressure. The reduced pressure may also be less than a hydrostatic pressure at a tissue site. Unless otherwise indicated, quantitative values of pressure stated herein are gauge pressures.

The reduced pressure delivered to the dressing bolster 114 may be constant or varied, patterned or random, and may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, unless otherwise indicated, an increase in reduced pressure or vacuum pressure may refer to a relative reduction in absolute pressure.

Continuing with FIG. 1, the reduced-pressure source 144 is shown as having a reservoir region 146, or canister region. An interposed membrane filter (not shown), such as hydrophobic or oleophobic filter, may be interspersed between the reduced-pressure delivery conduit 148 and the reduced-pressure source 144. One or more devices, such as a representative device 150, may be fluidly coupled to the reduced-pressure delivery conduit 148. The representative device 150 may be, for example, another fluid reservoir, a collection member to hold exudates and other fluids removed, a pressure-feedback device, a volume detection system, a blood detection system, an infection detection system, a flow monitoring system, or a temperature monitoring system. Multiple representative devices 150 may be included. One or more of the representative devices 150 may be formed integrally with the reduced-pressure source 144.

The reduced-pressure source 144 may be any device for supplying a reduced pressure, such as a vacuum pump, wall suction, or other source. While the amount and nature of reduced pressure applied to a tissue site may vary according to the application, the reduced pressure may be, for example, between about −5 mm Hg (−667 Pa) to about −500 mm Hg (−66.7 kPa). In some embodiments, the reduced pressure may be between about −75 mm Hg (−9.9 kPa) to about −300 mm Hg (−39.9 kPa).

The reduced pressure developed by the reduced-pressure source 144 may be delivered through the delivery conduit 148 to the conduit interface 138. The conduit interface 138 may allow the reduced pressure to be delivered through the sealing member 116 to the dressing bolster 114. In some embodiments, the conduit interface 138 may provide fluid communication external to the sealing member 116 without the application of reduced pressure.

The reduced-pressure indicator 101 may be configured to indicate that a reduced pressure of at least of certain threshold level is being delivered to the tissue site 102. The reduced-pressure indicator 101 may be a separate unit fluidly coupled to the sealing member 116 such that reduced pressure from within the sealed space of the sealing member 116 reaches the reduced-pressure indicator 101. In some embodiments, as shown in FIG. 1, the reduced-pressure indicator 101 may be associated with the conduit interface 138 as a part of the reduced-pressure assembly 140. When adequate reduced pressure is present, the reduced-pressure indicator 101 may be configured to assume a collapsed position. When inadequate reduced pressure is present, the reduced-pressure indicator 101 may be configured to assume a non-collapsed position.

Referring primarily to FIG. 2, the dressing assembly 112 may include a gasket member 117. The gasket member 117 may also be referred to interchangeably as an interface seal or sealing ring 117. For example, features or characteristics of the gasket member 117 may apply to the sealing ring 117, and features or characteristics of the sealing ring 117 may apply to the gasket member 117. The gasket member 117 and the sealing ring 117 may be configured in any suitable shape to enhance or otherwise provide a fluid seal around the tissue site 102, such as the incision 104. For example, the epidermis 106 may have recesses, cracks, wrinkles, or other discontinuities on a surface of the epidermis 106 that may cause leaks. Moreover, folds, buckles, wrinkles, or other discontinuities may form in the sealing member 116 and cause leaks. The gasket member 117 and the sealing ring 117 may help seal any such skin or sealing member discontinuities around the tissue site 102.

The gasket member 117 or the sealing ring 117 may be adapted to be positioned between the dressing assembly 112 and the epidermis 106 and/or the tissue site 102. In some examples, the gasket member 117 may be positioned on, coupled to, or directly coupled to the second side 122 of the dressing bolster 114 or the second side 128 of the comfort layer 124. The gasket member 117 or the sealing ring 117 may be formed, as an illustrative example, by applying or bonding a sealing material around a perimeter or circumference of a portion of the dressing assembly 112. Although the sealing material of the gasket member 117 or the sealing ring 117 may be configured in the shape of a ring in some embodiments, other shapes are suitable, and may include, without limitation, circles, squares, rectangles, discontinuous shapes, continuous shapes, irregular shapes, linear shapes, other shapes or portions that overlap one another, or combinations thereof. The sealing material may include hydrocolloids, hydrogels, silicone polymers (both crosslinked and uncrosslinked gels), and natural gums (xanthan, guar, cellulose). The sealing material may include other soft polymer gels, such as, for example, those based on polyurethanes, polyolefin gels, and acrylics.

In some embodiments, the gasket member 117 or the sealing ring 117 may be deployed by hand or extruded from an applicator, such as a syringe, to form a ring or other shape prior to application of the dressing assembly 112 to the tissue site 102. Sealing materials suitable for application by extrusion may include, without limitation, water soluble gums such as xanthan, guar, or cellulose, and thick greases, such as silicones. In another embodiment, the sealing ring 117 may be bonded in any suitable manner, such as, for example, by a heat bond, to the second, inward facing side 128 of the comfort layer 124 during manufacture of the dressing assembly 112. In at least this manner, the sealing ring 117 may be adapted to be positioned between the comfort layer 124 and the epidermis 106 and/or the tissue site 102.

In some embodiments, the gasket member 117 or the sealing ring 117 may include an absorbent. For example, the sealing ring 117 may be a hydrocolloid comprising an absorbent, such as carboxy methyl cellulose (CMC). The absorbent may permit the sealing ring 117 to absorb fluid from the tissue site 102 in addition to enhancing the fluid seal around the tissue site 102. The sealing ring 117 including the absorbent may enhance the ability of the dressing assembly 112 to manage and direct fluid away from the tissue site 102 for keeping the tissue site 102 dry. For example, the dressing bolster 114 may have a thickness between the first side 120 and the second, inward-facing side 122 of the dressing bolster 114. The thickness of the dressing bolster 114 may define at least a portion of a thickness of the dressing assembly 112. The sealing ring 117 may be adapted to be positioned between the dressing assembly 112 and the tissue site 102, as described above, and around or surrounding a circumference of the tissue site 102. Relative to the dressing assembly 112, the sealing ring 117 or the gasket member 117 may be positioned, for example, around, on, or at the lateral edges of the dressing bolster 114 and/or the comfort layer 124. Further, the sealing ring 117 or the gasket member 117 may extend beyond a lateral edge of the dressing bolster 114 and the comfort layer 124. Further, the sealing ring 117 may be positioned around or surrounding a circumference of the dressing bolster 114 and/or the comfort layer 124. Further, the sealing ring 117 may be positioned around at least a portion of the dressing bolster 114 or the comfort layer 124 that is configured to be positioned directly against or in direct contact with the tissue site 102. At least a portion of the dressing bolster 114 and/or the comfort layer 124 may be exposed and configured to be positioned directly against the tissue site 102 when the sealing ring 117 is positioned on the dressing assembly 112. Further, in such embodiments, the sealing ring 117 may surround the exposed portion of the dressing bolster 114 and/or the comfort layer 124.

The absorbent in the sealing ring 117 may wick or draw fluid in a lateral direction within the dressing assembly 112, normal to the thickness of the dressing bolster 114, and toward the lateral edges of the dressing bolster 114 for absorption in the sealing ring 117. Thus, fluid from the tissue site 102 may be wicked or otherwise drawn in a lateral direction along the surface of the tissue site 102 toward the lateral edges of the dressing bolster 114 and into the sealing ring 117. Further, fluid from the tissue site 102 may also flow through the thickness of the dressing assembly 112 and the dressing bolster 114 at least by operation of the manifold material comprising the dressing bolster 114, described above.

Referring again to FIGS. 1-2, the dressing assembly 112 may include a longitudinal axis 151 configured to be positioned along a longitudinal or lengthwise dimension of the tissue site 102, such as the incision 104, a linear wound, or any wound or tissue site having a lengthwise or longitudinal dimension that is greater than its width. In some embodiments, the treatment system 100 or the dressing assembly 112 may include a polymeric enhancement layer 153 configured to be positioned along or substantially aligned with the longitudinal axis 151 of the dressing assembly 112. The polymeric enhancement layer 153 may also be configured to be positioned along and in direct contact with a longitudinal or lengthwise dimension of the tissue site 102, such as the incision 104. Further, the polymeric enhancement layer 153 may be positioned on a side of the dressing assembly 112 configured to face toward the tissue site 102 such that the polymeric enhancement layer 153 is configured to be positioned between the dressing assembly 112 and the tissue site 102. For example, as shown in FIG. 2, in some embodiments, the polymeric enhancement layer 153 may be positioned on or coupled to the second side 128 of the comfort layer 124. In some embodiments (not shown), the polymeric enhancement layer 153 may be positioned on or coupled to the second side 122 of the dressing bolster 114 with the comfort layer 124 omitted or positioned around the polymeric enhancement layer 153 such that the polymeric enhancement layer 153 is configured to directly contact the tissue site 102.

The polymeric enhancement layer 153 may include a first side 156 a second side 158 positioned opposite or facing opposite to the first side 156. In some example embodiments, the first side 156 of the polymeric enhancement layer 153 may be coupled to the second side 128 of the comfort layer 124. The second side 158 of the polymeric enhancement layer 153 may be configured to directly contact the tissue site 102, such as the incision 104. In some examples, at least a portion of the comfort layer 124 may be exposed around a periphery 160 of the polymeric enhancement layer 153 to form an exposed surface 162. The exposed surface 162 of the comfort layer 124 may be configured to be positioned directly against the tissue site 102. In such an example, both the comfort layer 124 and the polymeric enhancement layer 153 may be configured to directly contact the tissue site 102. Further, the sealing ring 117 or the gasket member 117 may be positioned around the exposed surface 162 of the comfort layer 124. Although not shown, in some examples, the polymeric enhancement layer 153 may cover the second side 128 of the comfort layer 124 entirely.

In some examples, the polymeric enhancement layer 153 may include or be formed of at least one strip 164 of material that may be substantially aligned along the longitudinal axis 151 of the dressing assembly 112. The at least one strip 164 may have a length 161 and a width 163 perpendicular to the length 161. In some examples, the length 161 may extend along the longitudinal axis 151 of the dressing assembly 112 between about 5 inches to about 10 inches, and the width 163 may be between about 0.5 inches to about 2 inches. Further, in some examples, the at least one strip 164 may include a plurality of strips 164. Further, in some examples, the second side 158 of the polymeric enhancement layer 153 may comprise an acrylic material, a silicone material, or both an acrylic and a silicone material configured to directly contact the tissue site 102, and more specifically, the incision 104.

Figure 5:
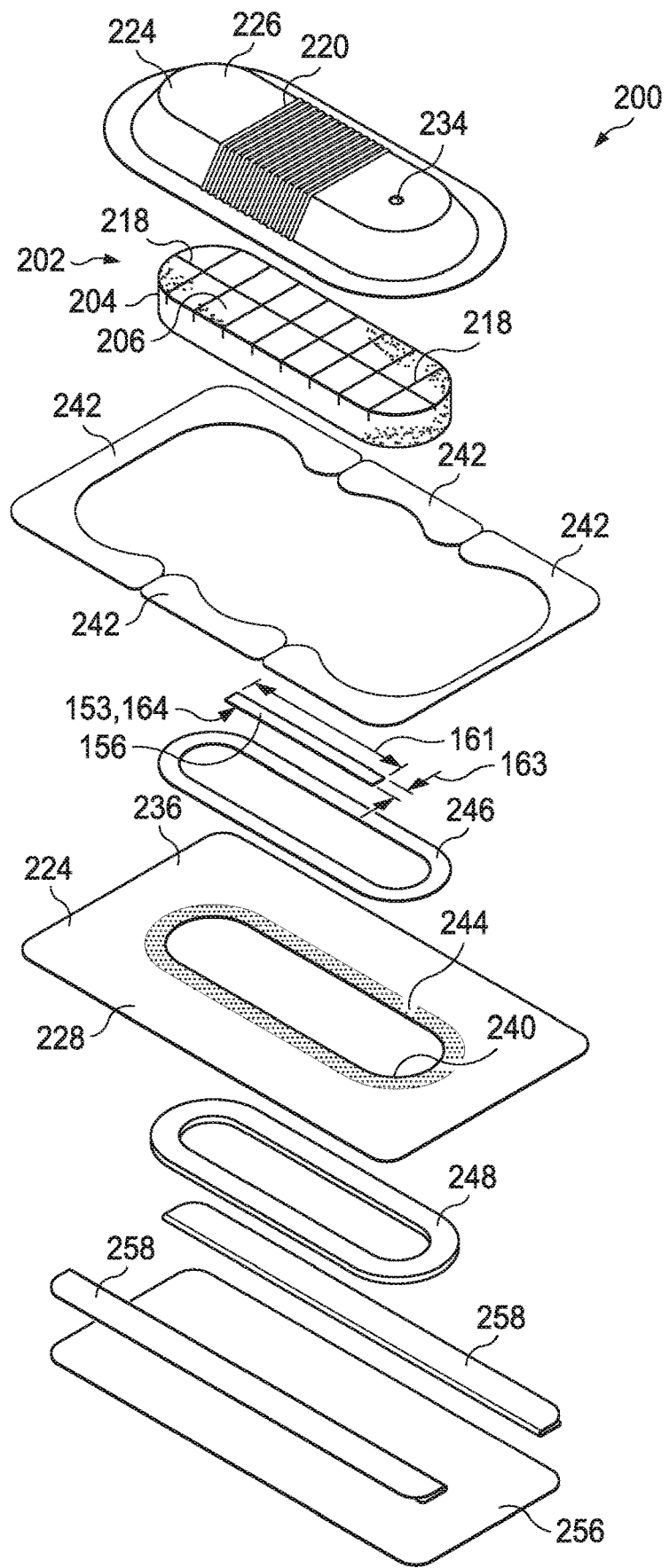
FIG. 5 is an exploded, perspective view of the example dressing assembly of FIG. 4 in a state prior to assembly or deployment at a tissue site.

Referring now primarily to FIGS. 3-5, depicted is a portion of an illustrative embodiment of a treatment system 200 suitable for treating, for example, a linear wound, area wound, a graft, or other wound. FIGS. 3-5 depict the treatment system 200 in a pre-deployment state. The treatment system 200 may include a dressing assembly 202, and the dressing assembly 202 may include a dressing bolster 204. The dressing bolster 204 has a first side 206 and a second, inward-facing side 208. The dressing bolster 204 may be formed from any suitable bolster material, or manifold material, as previously referenced in connection with the dressing bolster 114. A comfort layer 210, which has a first side 212 and a second, inward-facing side 214, may be coupled, such as, for example, by a heat bond 216 or other suitable technique to the second, inward-facing side 208 of the dressing bolster 204.

The comfort layer 210 may be any material that helps prevent skin irritation and discomfort while allowing fluid transmission through the comfort layer 210. Suitable materials for the comfort layer 210 have been mentioned in connection with the comfort layer 124 of FIGS. 1-2. In some embodiments, the comfort layer 210 may include antimicrobial substances, such as silver. Further, in some embodiments, the comfort layer 210 may be made as a breathable, dry layer.

In some illustrative embodiments, the dressing bolster 204 may include a plurality of flexibility notches 218. The flexibility notches 218 may extend partially through or completely through the dressing bolster 204. The flexibility notches 218 may be lateral notches, or lateral cuts, in the dressing bolster 204. The flexibility notches 218 may also be one or more longitudinal notches, longitudinal cuts, or other cuts. The cuts may be made using a saw, a notched blade, a hot knife, or other device. The flexibility notches 218 may enhance the flexibility of the dressing bolster 204. The enhanced flexibility may be particularly useful when the dressing assembly 202 is applied over a joint or other area of movement on a patient. For example, if the dressing bolster 204 is used on a knee, the dressing bolster 204 may need to flex or extend as much as 100% or more. The flexibility notches 218 may provide such flexibility.

The dressing bolster 204 may have lateral edges 205 that are orthogonal with respect to the second, inward-facing side 208 of the dressing bolster 204. The lateral edges 205 may also have a shape, such as, for example, a beveled, angled, or rounded shape. The lateral edges 205, when angled, may be between about 10 degrees to about 90 degrees with respect to the second, inward-facing side 208 of the dressing bolster 204. The shaped lateral edges 205 may reduce shear stress between an epidermis of a patient and the dressing bolster 204. Other dimensions, steps, and processes may be used.

In some illustrative embodiments, the dressing bolster 204 may be manufactured from a foam block of GRANUFOAM™ material. The GRANUFOAM™ material may be, for example, a foam block having the dimensions of 1.21 meters×1.8 meters×0.5 meters. The foam block may be cut to have a 19 millimeter height, and a saw may be used to form lateral grooves, such as the flexibility notches 218, in the foam block. A dry layer, such as the comfort layer 210, may be laminated or otherwise attached to the second, inward facing side 208 of the dressing bolster 204. The foam block may be cut, for example, utilizing a die cutter to form a plurality of individual dressing bolsters 204.

A sealing subsystem 222 may provide a fluid seal over the dressing assembly 202 and at least a portion of an epidermis of a patient. The sealing subsystem 222 may include a sealing member 224. The sealing member 224 may be formed with an upper drape portion or first sealing member portion 226 and a lower drape portion or second sealing member portion 228. The first sealing member portion 226 may extend over or cover the first side 206 of the dressing bolster 204 to form a drape flange, or drape extension 230. The drape extension 230 has a first side 232 and a second, inward-facing side 233. The second, inward-facing side 233 of the drape extension 230 may be adapted to face a tissue site of a patient as described above. An aperture 234 may be formed on the first sealing member portion 226. The aperture 234 may provide fluid communication with a conduit interface (not shown). The conduit interface may be analogous to the conduit interface 138 in FIG. 1.

The second sealing member portion 228 may have a first side 236 and a second, inward-facing side 237 adapted to face a tissue site as described above. The second, inward-facing side 233 of the drape extension 230 may be placed on the first side 236 of the second sealing member portion 228, and may be coupled to the first side 236 by an attachment device 238. The attachment device 238 may be, for example, an adhesive, a bond, a weld (e.g., ultrasonic or RF weld), cements, stitching, staples, or other coupling device. The second sealing member portion 228 may include an attachment apparatus on the second, inward-facing side 237 as described below. The second sealing member portion 228 may also include a treatment area aperture 240, depicted in FIG. 5, that may be adapted to permit fluid communication through the second sealing member portion 228 and, for example, between a tissue site and the dressing bolster 204. The treatment area aperture 240 may also provide an opening for at least a portion of the dressing bolster 204, or the comfort layer 210, to be positioned directly against an epidermis and/or a tissue site of a patient.

The first sealing member portion 226 may include a plurality of folds 220 or bellows to facilitate movement as described above. The folds 220 may allow the first sealing member portion 226 to expand. For example, if the dressing assembly 202 is used on a joint, when the joint is flexed, additional drape material from the folds 220 may be released to facilitate movement of the first sealing member portion 226. The folds 220 may also be formed as ridges having the cross-sectional shape of an accordion that provides additional drape material when flattened or stretched, for example.

One or more release members 242 may be releasably coupled to the first side 236 of the second sealing member portion 228, such as, for example, with an adhesive (not shown) applied on at least a portion of the first side 236. Four of the release members 242 are shown in the illustrative embodiment of FIG. 3. The release members 242 may provide stiffness to the second sealing member portion 228, and may cover the adhesive or other attachment apparatus to provide a grasping surface during deployment of the dressing assembly 202. The release members 242 may be casting paper or a film held on the first side 236 of the second sealing member portion 228.

The first side 236 of the second sealing member portion 228 may include an adhesive 244 adapted to retain the second side 208 of the dressing bolster 204 against the second sealing member portion 228 during assembly and usage. A center release member 246 may cover and protect the adhesive 244 prior to assembly. The release members 242 that may provide stiffness to the sealing member 224 during deployment may be positioned outboard of the adhesive 244 on the first side 236 of the second sealing member portion 228.

The dressing assembly 202 may include a sealing ring 248. Analogous to the sealing ring 117, the sealing ring 248 may help seal any wrinkles or discontinuities in the epidermis or drape that might otherwise cause leaks. Also analogous to the sealing ring 117, the sealing ring 248 may also be referred to interchangeably as an interface seal or a gasket member 248. For example, features or characteristics of the gasket member 248 may apply to the sealing ring 248, and features or characteristics of the sealing ring 248 may apply to the gasket member 248. Further, the previously described features of the sealing ring 117 or the gasket member 117 associated with the dressing assembly 112 may apply by analogy to the sealing ring 248 or the gasket member 248 associated with the dressing assembly 202.

The sealing ring 248 or the gasket member 248 may be, for example, positioned to cover a portion of the second, inward-facing side 237 of the second sealing member portion 228. The sealing ring 248 or the gasket member 248 may be coupled directly to the dressing assembly 202, or coupled with an optional sealing-ring attachment device 249, such as an acrylic adhesive, cement, or other coupling device. In other embodiments, the sealing ring 248 or the gasket member 248 may be coupled to the second inward-facing side 208 of the dressing bolster 204, and/or to an adjacent layer, such as the comfort layer 210.

The sealing ring 248 or the gasket member 248 may straddle an edge of the dressing bolster 204, or otherwise extend beyond an edge of the dressing bolster 204, as depicted in FIG. 4. In some embodiments, the sealing ring 248 or the gasket member 248 may be coupled to a portion of the sealing member 224, such as the first sealing member 226 and/or the second sealing member 228. In some embodiments, the dressing bolster 204 may entirely overlap the sealing ring 248 or the gasket member 248 as suggested in FIG. 11. While reference is made to a "ring," discrete members, including linear members, may make up the sealing ring 248 or the gasket member 248.

The sealing ring 248 may comprise a sealing material, such as, for example, any of the sealing materials previously described in connection with the sealing ring 117, or other material that provides initial tack between the dressing assembly 202 and an epidermis of a patient. Further, the sealing ring 248 may have a durometer, such as a material softness or hardness, between about 20 Shore 00 to about 90 Shore OO. In some embodiments, the durometer of the sealing ring 248 may be between about 70 Shore 00 to about 80 Shore OO. The sealing ring 248 may have a modulus of elasticity that falls between the modulus of elasticity of the second sealing member portion 228 and the modulus of elasticity of a tissue site and/or epidermis of a patient. As shown in FIG. 4, the sealing ring 248 may have a thickness 250 and a width 252. The thickness 250 of the sealing ring 248 may be between about 0.3 millimeters to about 2.5 millimeters. In some embodiments, the thickness 250 may be between about 0.7 millimeters to about 1.25 millimeters. The width 252 of the sealing ring 248 may be between about 10 millimeters to about 30 millimeters. Other dimensions are possible. In some illustrative embodiments, the thickness 250 may be about 0.7 millimeters and the width 252 may be about 20 millimeters. Further, in some embodiments, the width 252 of the sealing ring 248 may extend beyond an edge of the dressing bolster 204 by about 10 millimeters and overlap the dressing bolster 204 by about 10 millimeters.

In some embodiments, the second sealing member portion 228 may have a thickness 229 between about 0.178 millimeters to about 0.254 millimeters, or about 7 mils to about 10 mils. The ratio of the sealing ring thickness 250 to the sealing member thickness 229 may be between about 2.75 to about 7.03.

The sealing ring 248 may include fenestrations or apertures. In some embodiments, the sealing ring 248 may comprise a patterned sealing material on the second, inward-facing side 214 of the comfort layer 210, or on the second, inward-facing side 208 of the dressing bolster 204. The pattern may be, for example, spaced islands, crossing lines of sealing material, or any other suitable pattern.

The sealing ring 248 may function as a two-sided gasket that may provide a seal between the dressing assembly 202 and a tissue site and/or epidermis of a patient. For example, the sealing ring 248 may provide a seal between the dressing bolster 204, the comfort layer 210, or the second sealing member portion 228 and a tissue site and/or epidermis of a patient. The sealing ring 248 may absorb perspiration or other fluids from a tissue site. Further, the sealing ring 248 may help distribute shear forces created, for example, by the application of reduced pressure at the interface of the dressing bolster 204 and a tissue site and/or epidermis of a patient.

Analogous to the dressing assembly 112, the dressing assembly 202 shown in FIGS. 4-5 may include the longitudinal axis 151 configured to be positioned along a longitudinal or lengthwise dimension of the tissue site 102, such as the incision 104, a linear wound, or any wound or tissue site having a lengthwise or longitudinal dimension that is greater than its width. In some embodiments, the treatment system 200 or the dressing assembly 202 may include the polymeric enhancement layer 153 configured to be positioned along or substantially aligned with the longitudinal axis 151 of the dressing assembly 202. The polymeric enhancement layer 153 may also be configured to be positioned along and in direct contact with a longitudinal or lengthwise dimension of the tissue site 102, such as the incision 104. Further, the polymeric enhancement layer 153 may be positioned on a side of the dressing assembly 202 configured to face toward the tissue site 102 such that the polymeric enhancement layer 153 is configured to be positioned between the dressing assembly 202 and the tissue site 102. For example, as shown in FIG. 4, in some embodiments, the polymeric enhancement layer 153 may be positioned on or coupled to the second side 214 of the comfort layer 210. In some embodiments (not shown), the polymeric enhancement layer 153 may be positioned on or coupled to the second side 208 of the dressing bolster 204 with the comfort layer 210 omitted or positioned around the polymeric enhancement layer 153 such that the polymeric enhancement layer 153 is configured to directly contact the tissue site 102. In some example embodiments, the first side 156 of the polymeric enhancement layer 153 may be coupled to the second side 214 of the comfort layer 210. The second side 158 of the polymeric enhancement layer 153 may be configured to directly contact the tissue site 102, such as the incision 104.

Further, analogous to the comfort layer 124, at least a portion of the comfort layer 210 may be exposed around the periphery 160 of the polymeric enhancement layer 153 to form the exposed surface 162 such that both the comfort layer 210 and the polymeric enhancement layer 153 may be configured to directly contact the tissue site 102. Further, the sealing ring 248 or the gasket member 248 may be positioned around the exposed surface 162 of the comfort layer 210.

As shown in FIG. 4, a portion of the second, inward-facing side 237 of the second sealing member portion 228 may be covered with a sealing apparatus or device 254, such as an adhesive. With reference to FIGS. 4 and 5, when in the pre-deployment state, the sealing device 254 may be covered by a bottom release member 256 and side release members 258.

The bottom release member 256 may cover and protect, for example, the sealing device 254 and the sealing ring 248. The side release members 258 may also cover and protect the sealing device 254. Similar to the release members 242, the side release members 258 may provide a grasping surface for a user to facilitate deployment of the dressing assembly 202. The release members 242, the bottom release member 256, and/or the side release members 258 may be comprised of a polar semi-crystalline polymer, such as, for example, polyethylene terephthalate (PET). Use of a polar semi-crystalline polymer for the release members 242, the bottom release member 256, and/or the side release members 258 may substantially preclude wrinkling or other deformation of the dressing assembly 202. Any deformation of the release members 242, the bottom release member 256, and/or the side release members 258 may cause wrinkling or deformation of a component of the dressing assembly 202. The polar semi-crystalline polymer is highly orientated and resistant to softening, swelling, or other deformation that may occur when brought into contact with components of the dressing assembly 202, or when subjected to temperature or environmental variations, or sterilization. Thus, for example, when the polar semi-crystalline polymer is used in combination with the hydrocolloid described above for the sealing ring 248, the polar semi-crystalline polymer may not deform when in contact with the compounding ingredients of the hydrocolloid. In some embodiments, the release members 242, the bottom release member 256, and/or the side release members 258 may be configured to resist deformation when exposed to temperature variations between about 40 degrees Celsius to about 60 degrees Celsius, and gamma sterilization doses between about 25 kGy to about 45 kGy.

Continuing with FIGS. 3-5, according to an illustrative embodiment of operation, the bottom release member 256 may be removed to expose the sealing device 254 on the second, inward-facing side 237 of the second sealing member portion 228. Removal of the bottom release member 256 may also expose a second, inward-facing surface 247 of the sealing ring 248. The sealing device 254 and/or the second, inward-facing surface 247 of the sealing ring 248 may be placed against a portion of an epidermis of a patient and around a tissue site that may include a linear wound as described above. The side release members 258 may be removed after applying the second sealing member portion 228. Similarly, the release members 242 on the first side 236 of the second sealing member portion 228 may be removed after applying the second sealing member portion 228. A conduit interface may be coupled to the aperture 234 in the first sealing member portion 226, and reduced pressure may be delivered to the dressing assembly 202.

Regarding the manufacture of the systems and components described above, in applying and coupling a sealing member to a dressing bolster, a press may be utilized to remove any wrinkles in the sealing member. Further, the medical bolster material of the shaped dressing assembly may be cut using a die cutter, or by hand with a router.

Figure 6A:
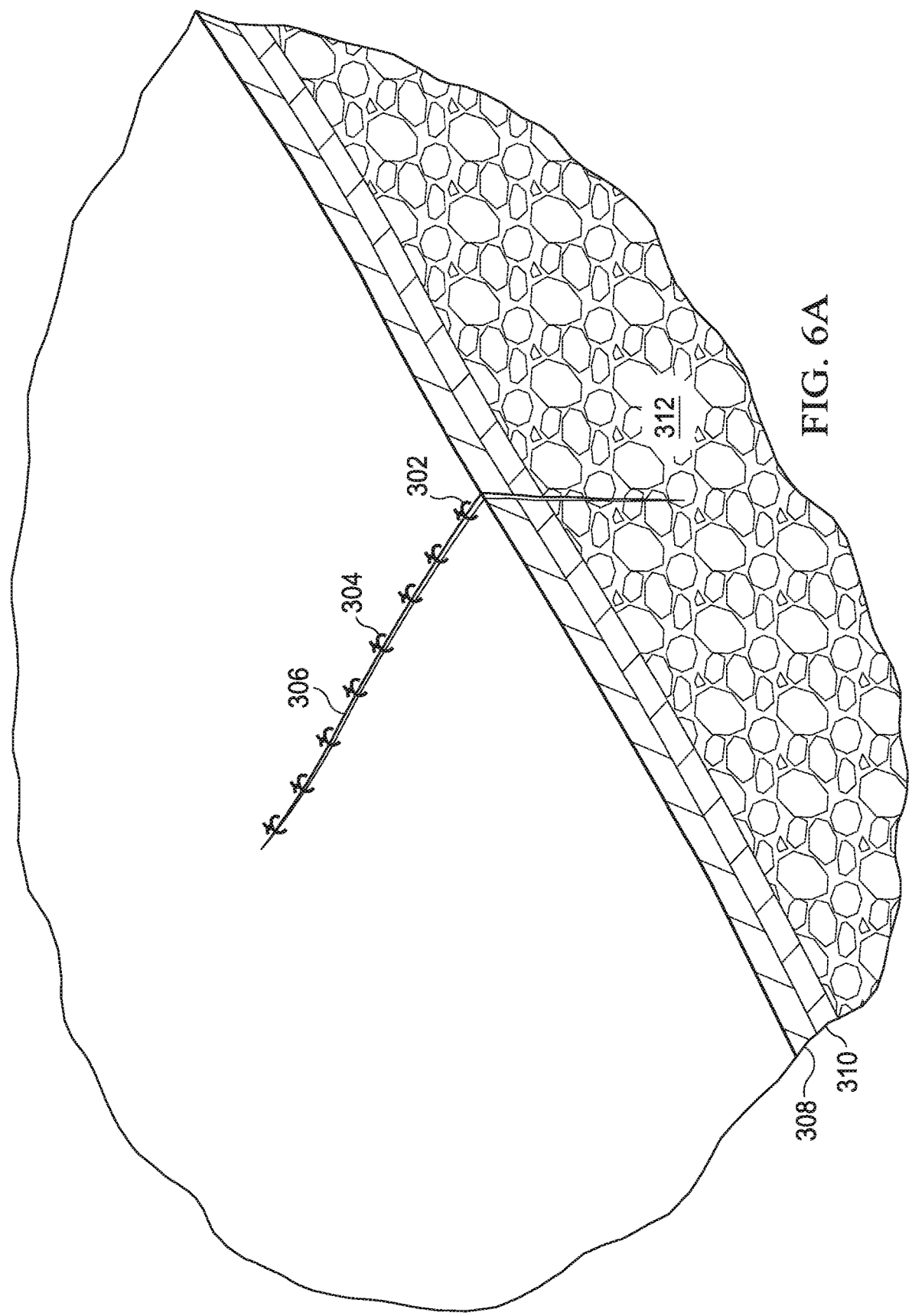
FIGS. 6A-6C are perspective views, with a portion shown in cross-section, of a portion of an illustrative example embodiment of a treatment system being deployed over a linear wound.
Figure 6B:
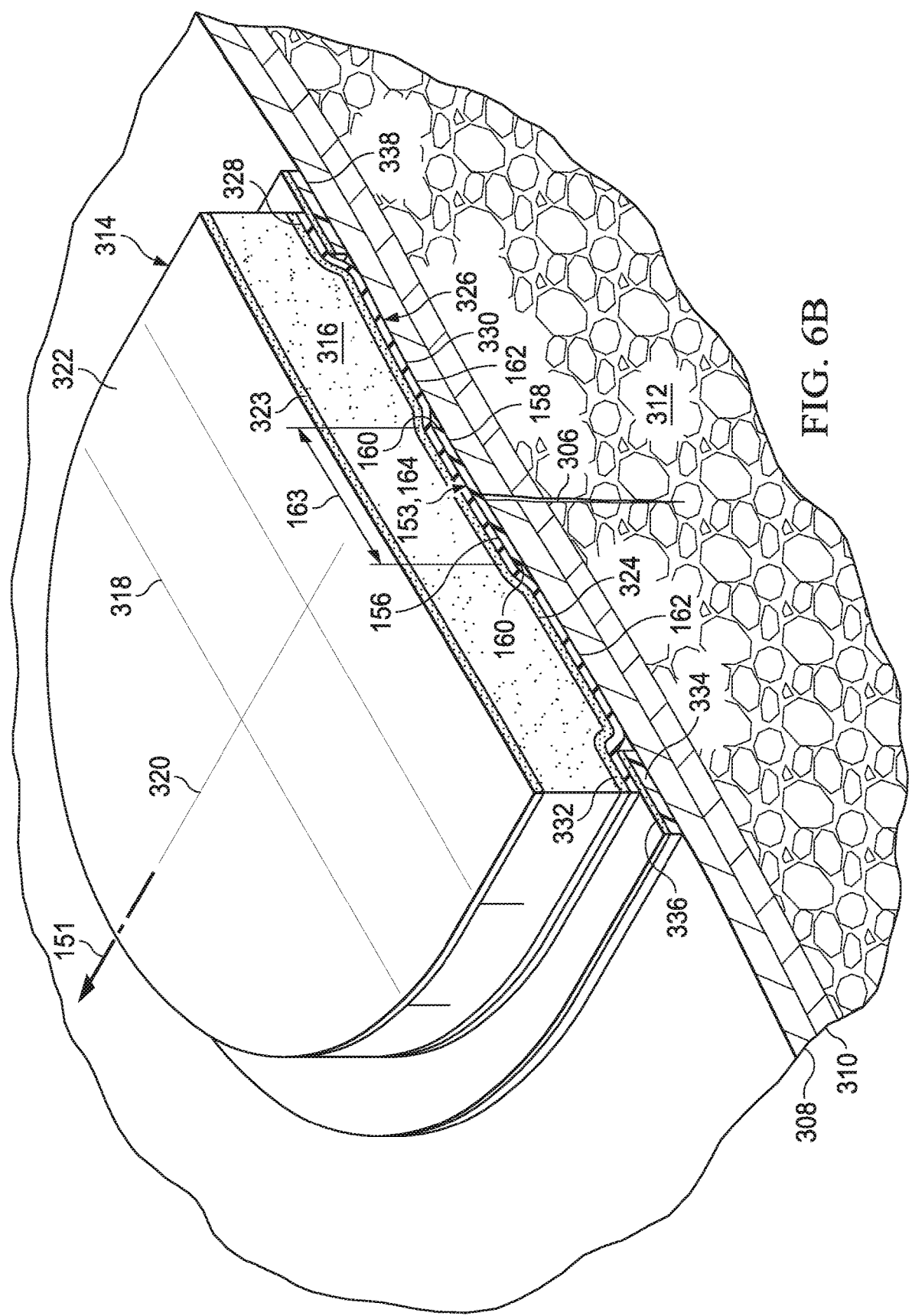
Figure 6C:
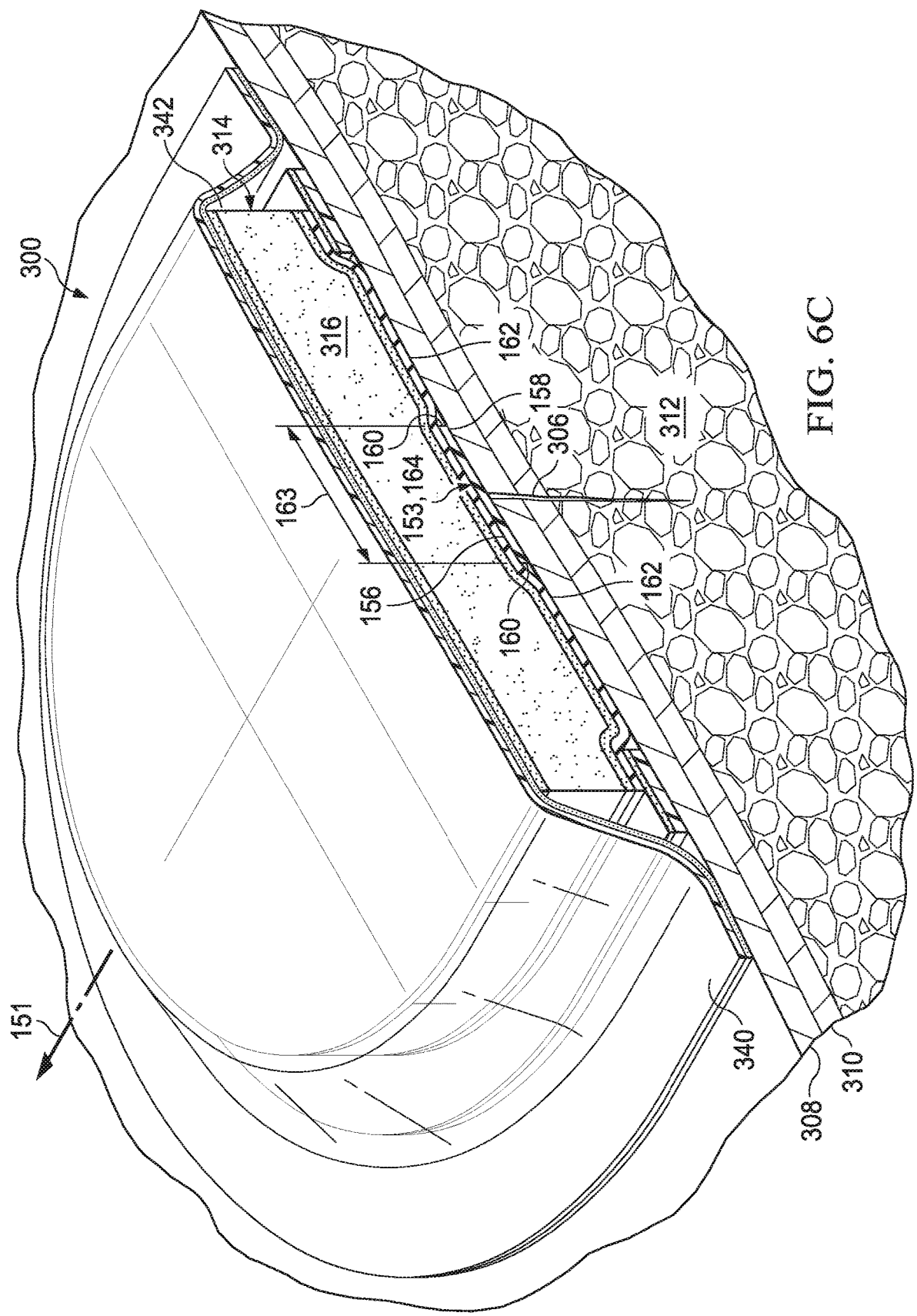

Referring now primarily to FIGS. 6A-6C, presented is another illustrative embodiment of a portion of a treatment system 300. FIGS. 6A-6C depict the treatment system 300 assembled in stages at a tissue site, such as a linear wound 306. In FIG. 6A, a closure device 302, such as, for example, stitches 304, close the linear wound 306. Other closure devices 302, such as epoxy or staples may be utilized to close the linear wound 306. The linear wound 306 may include a portion through an epidermis 308, dermis 310, and subcutaneous tissue 312 of a patient.

Referring now to FIG. 6B, after the linear wound 306 is closed or prepared as described above, a dressing assembly 314 may be disposed proximate to the linear wound 306. The dressing assembly 314 may include a dressing bolster 316. The dressing bolster 316 may be formed from the bolster or manifold materials previously mentioned. The dressing bolster 316 may include a plurality of lateral notches 318 and one or more longitudinal notches 320. The dressing bolster 316 has a first side 322 and a second, inward-facing side 324. The first side 322 may include an adhesive layer 323. The adhesive layer 323 may help secure a sealing member 340 thereto, as shown in FIG. 6C.

The dressing assembly 314 may include a comfort layer 326. The second, inward-facing side 324 of the dressing bolster 316 may be covered with the comfort layer 326. The comfort layer 326 has first side 328 and a second, inward-facing side 330. The first side 328 of the comfort layer 326 may be coupled by an attachment device 332, such as, for example, a heat bond, adhesive, weld, or other attachment device, to the second, inward-facing side 324 of the dressing bolster 316.

The dressing assembly 314 may include a sealing ring 334. The sealing ring 334 may be coupled, at least in part, to the second, inward-facing side 330 of the comfort layer 326. The sealing ring 334 may be analogous to the sealing ring 117 of FIG. 2 and the sealing ring 248 of FIGS. 3-5. Further, the sealing ring 334 may be referred to interchangeably as a gasket member 334 analogous to the gasket member 117 and the gasket member 248.

The sealing ring 334 may comprise any of the sealing materials previously described in connection with the sealing ring 117 and the sealing ring 248. The sealing ring 334 may adhere directly to the comfort layer 326, or may be coupled with a sealing-ring attachment device 336 to the comfort layer 326. The sealing-ring attachment device 336 may be, for example, acrylic adhesive, cement, or other suitable attachment device. The sealing ring 334 and/or the sealing ring attachment device 336 may be co-extensive with the comfort layer 326, or may extend beyond a lateral edge of the comfort layer 326 and the dressing bolster 316.

Analogous to the dressing assembly 112 and the dressing assembly 202, the dressing assembly 314 may include the longitudinal axis 151 configured to be positioned along a longitudinal or lengthwise dimension of a tissue site, such as a linear wound 306, or any wound or tissue site having a lengthwise or longitudinal dimension that is greater than its width. In some embodiments, the treatment system 300 or the dressing assembly 314 may include the polymeric enhancement layer 153 configured to be positioned along or substantially aligned with the longitudinal axis 151 of the dressing assembly 314. The polymeric enhancement layer 153 may also be configured to be positioned along and in direct contact with a longitudinal or lengthwise dimension of the linear wound 306. Further, the polymeric enhancement layer 153 may be positioned on a side of the dressing assembly 314 configured to face toward the linear wound 306 such that the polymeric enhancement layer 153 is configured to be positioned between the dressing assembly 314 and the linear wound 306. For example, as shown in FIGS. 6B-6C, in some embodiments, the polymeric enhancement layer 153 may be positioned on or coupled to the second side 330 of the comfort layer 326. In some embodiments (not shown), the polymeric enhancement layer 153 may be positioned on or coupled to the second side 324 of the dressing bolster 316 with the comfort layer 326 omitted or positioned around the polymeric enhancement layer 153 such that the polymeric enhancement layer 153 is configured to directly contact the linear wound 306. In some example embodiments, the first side 156 of the polymeric enhancement layer 153 may be coupled to the second side 330 of the comfort layer 326. The second side 158 of the polymeric enhancement layer 153 may be configured to directly contact a tissue site, such as the linear wound 306.

Further, analogous to the comfort layer 124 and 210, at least a portion of the comfort layer 326 may be exposed around the periphery 160 of the polymeric enhancement layer 153 to form the exposed surface 162 such that the polymeric enhancement layer 153 may be configured to directly contact the linear wound 306, and the comfort layer 326 may be configured to directly contact a portion of the tissue site around the linear wound 306. Further, the sealing ring 334 or the gasket member 334 may be positioned around the exposed surface 162 of the comfort layer 326.

Prior to application, a second, inward-facing surface 338 of the sealing ring 334 may be covered by a release member or release liner (not shown). When the release liner is removed, the sealing ring 334 may be centered about the linear wound 306 for deployment. A release member or release liner (not shown) may also temporarily cover a portion of the sealing ring 334 and/or sealing ring attachment device 336 to provide a grasping surface during deployment of the dressing assembly 314. The release liner or release member covering, for example, the sealing ring 334, the sealing ring attachment device 336, and/or other components of the dressing assembly 314 may be analogous to the release members 242, 256, and 258 of FIGS. 3-5. For example, the release members may be positioned on the dressing assembly 314 analogous to the release members 242, 256, and 258. Further, the release members on the dressing assembly 314 may be comprised of any of the materials previously described for the release members 242, 256, and 258, such as, for example, a polar semi-crystalline polymer or polyethylene terephthalate (PET). As described above, use of a polar semi-crystalline polymer such as PET as a release member on the dressing assembly 314 may substantially preclude deformation of the dressing assembly 314. In another embodiment, the sealing ring 334 may be separately applied around the linear wound 306 before the dressing bolster 316 is applied thereto.

Referring now to FIG. 6C, a sealing member 340 may be disposed over the dressing assembly 314 and a portion of the epidermis 308 to form a sealed space 342 between the dressing assembly 314 and the linear wound 306. Analogous to the aperture 234 in FIG. 3, an aperture (not shown) may be formed or preformed in the sealing member 340. A conduit interface (not shown), analogous to conduit interface 138 described above, may be coupled to the sealing member 340 to provide fluid communication with the sealed space 342 through the aperture. Further, a reduced-pressure source (not shown), analogous to the reduced-pressure source 144 in FIG. 1, may be coupled to the conduit interface to provide reduced pressure to the sealed space 342 to treat the linear wound 306. A delivery conduit (not shown), analogous to the delivery conduit 148 in FIG. 1, may be utilized for coupling the reduced pressure source to the conduit interface. Reduced pressure may be applied to the tissue site, such as the linear wound 306, and fluid may be extracted from the tissue site and into the dressing assembly 314. The fluid from the tissue site may be absorbed into the sealing ring 334. The fluid from the tissue site may be wicked or otherwise communicated in a lateral direction within the dressing assembly 314 toward the sealing ring 334.

Referring to FIGS. 7-9D, the polymeric enhancement layer 153 may include various example features. In some examples, the polymeric enhancement layer 153 may include an exposed pattern of silicone material 166 and/or acrylic material 168. In various embodiments, the silicone material 166, the acrylic material 168, or both the silicone material 166 and the acrylic material 168 may be configured to directly contact a tissue site. In some example embodiments, without limitation, the acrylic material 168 may be an acrylic adhesive, and the silicone material 166 may be a silicone adhesive. Further, in some examples, the silicone material may be, without limitation, a silicone gel, a cured or completely cured silicone adhesive having minimal or no tack, and/or a multiple silicone gels including different hydrophilicity.

Figure 7:
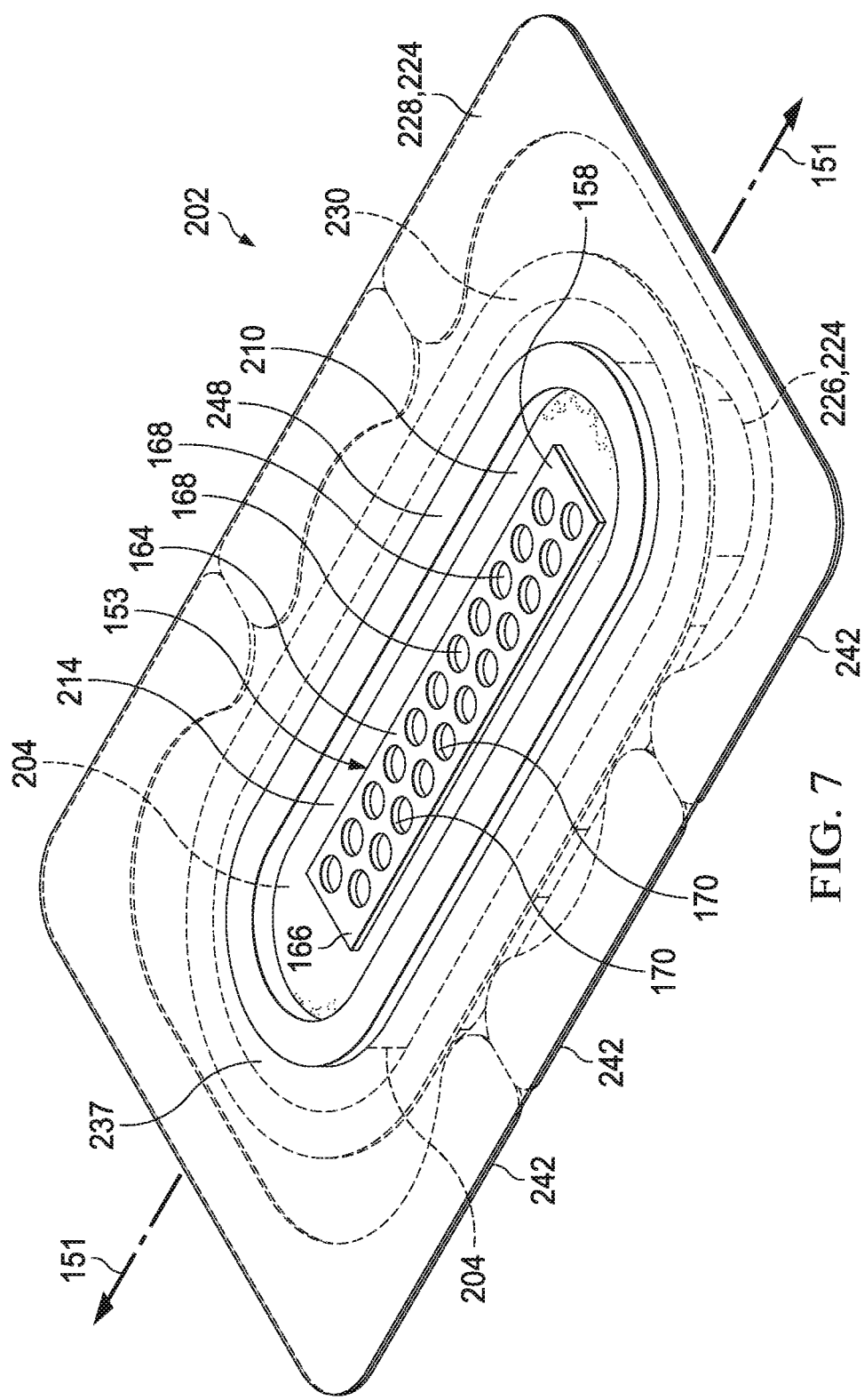
FIG. 7 is a perspective view of a bottom surface of an illustrative example embodiment of a dressing assembly.
Figure 8:
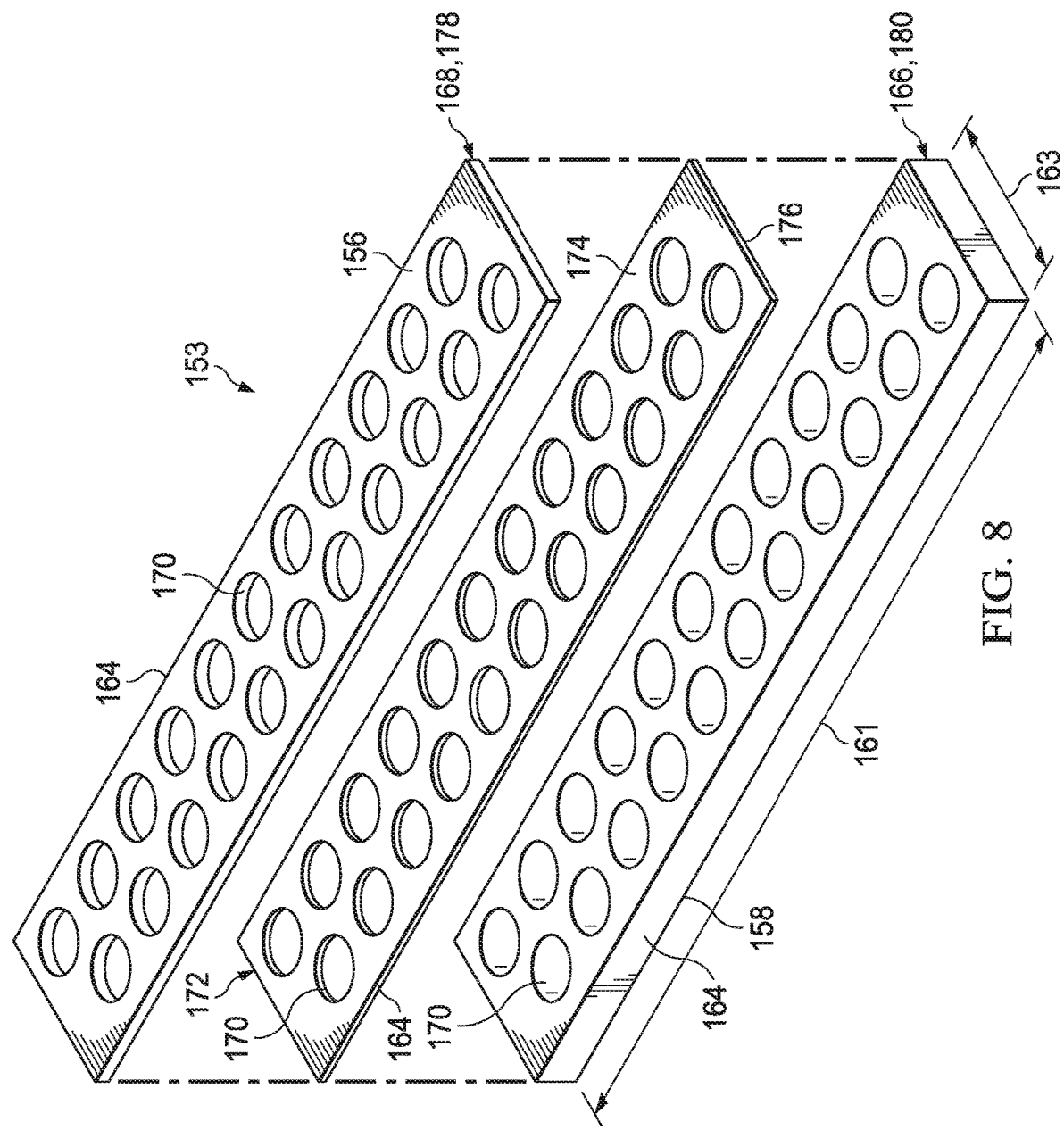
FIG. 8 is a perspective, exploded view of an illustrative example embodiment of a polymeric enhancement layer depicted in FIG. 7.

Referring to FIGS. 7-8, the polymeric enhancement layer 153 may include a plurality of apertures 170 disposed through the polymeric enhancement layer 153 between the first side 156 and the second side 158 of the polymeric enhancement layer 153. In some example embodiments, the plurality of apertures 170 may be configured to be in fluid communication or to provide fluid communication between the second side 128, 214, 330 of the comfort layer 124, 210, 326 and a tissue site. Further, the plurality of apertures 170 may be configured to be in fluid communication or to provide fluid communication between the second side 128, 214, 330 of the comfort layer 124, 210, 326 and the second side 158 of the polymeric enhancement layer 153. Although the apertures 170 are illustrated as having a circular shape, other shapes and types of apertures may be suitable, such as, without limitation, slits, slots, fenestrations, holes, rectangular shapes, triangular shapes, linear shapes, square shapes, and others.

Referring to FIG. 8, in some examples, the polymeric enhancement layer 153 may include a film layer 172 having a first side 174 and a second side 176 opposing or positioned opposite to the first side 174. Examples of suitable materials for the film layer 172 may be, without limitation, polyurethane and polyester. Further, in some examples, the acrylic material 168 or acrylic adhesive may be configured as an acrylic layer 178. The acrylic layer 178 may be positioned on the first side 174 of the film layer 172 and configured to be coupled to the second side 128, 214, 330 of the comfort layer 124, 210, 326. Similarly, in some examples, the silicone material 166 or silicone adhesive may be configured as a silicone layer 180. The silicone layer 180 may be positioned on the second side 176 of the film layer 172 and configured to be positioned in direct contact with a tissue site, such as the tissue site 102 or the linear wound 306. In such an example, the acrylic layer 178 may form at least a portion of the first side 156 of the polymeric enhancement layer 153, and the silicone layer 180 may form at least a portion of the second side 158 of the polymeric enhancement layer 153. Further, the plurality of apertures 170 may be disposed through the film layer 172, the acrylic layer 178, and the silicone layer 180 from the first side 156 to the second side 158 of the polymeric enhancement layer 153.

In some example embodiments, a portion of the acrylic material 168 on the first side 156 of the polymeric enhancement layer 153 may be exposed on the second side 158 of the polymeric enhancement layer 153 through at least one of the apertures 170 and configured to be in direct contact with a tissue site, such as the tissue site 102 or the linear wound 306. Although the acrylic material 168 may be exposed through the silicone material 166 in some examples, the configuration may be reversed in other examples such that the silicone material 166 is exposed through the acrylic material 168 in an analogous manner. In other example embodiments, the acrylic material 168 may not be exposed. For example, the acrylic material 168 may only be configured to couple the first side 156 of the polymeric enhancement layer 153 to the second side 128, 214, 330 of the comfort layer 124, 210, 326. In such an example, the apertures 170 may remain open without the acrylic material 168 being exposed through the apertures 170.

Further, in some examples, the film layer 172 may be omitted. In such an example, the silicone layer 180 may include the plurality of apertures 170 disposed through the silicone layer 180, and the acrylic layer 178 may be positioned between the second side 128, 214, 330 of the comfort layer 124, 210, 326 and the silicone layer 180. In such an example, a portion of the acrylic layer 178 may be exposed through the apertures 170 in the silicone layer 180 such that a portion of both the acrylic layer 178 and the silicone layer 180 may form the second side 158 of the polymeric enhancement layer 153 that is configured to be in direct contact with a tissue site. Alternatively, the acrylic layer 178 may not be exposed through the apertures 170, and instead, may only be configured to secure or couple the silicone layer 180 to the second side 128, 214, 330 of the comfort layer 124, 210, 326 such that only the silicone layer 180 forms the second side 158 of the polymeric enhancement layer 153.

Further, in some examples, the exposed pattern on the second side 158 of the polymeric enhancement layer 153 may be dots of the acrylic material 168 without the silicone material 166, dots of the silicone material 166 without the acrylic material 168, or dots of both the acrylic material 168 and the silicone material 166 applied to a substrate material. For example, the first side 174 of the film layer 172 may be configured to be coupled to the second side 128, 214, 330 of the comfort layer 124, 210, 326, and one or both of the silicone material 166 and the acrylic material 168 may be positioned on the second side 176 of the film layer 172 and configured to face a tissue site, such as the tissue site 102 or the linear wound 306.

Figure 9D:
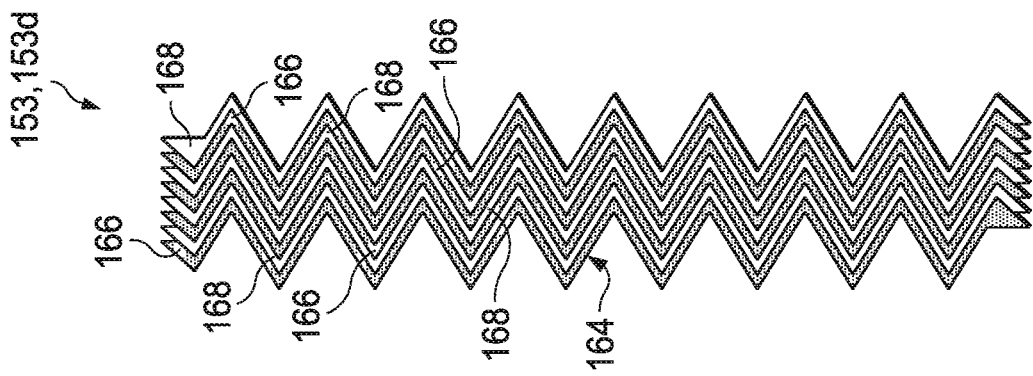
FIGS. 9A-9D are plan views of multiple illustrative example embodiments of polymeric enhancement layers suitable for use with a dressing assembly and system according to this disclosure.
Figure 9C:
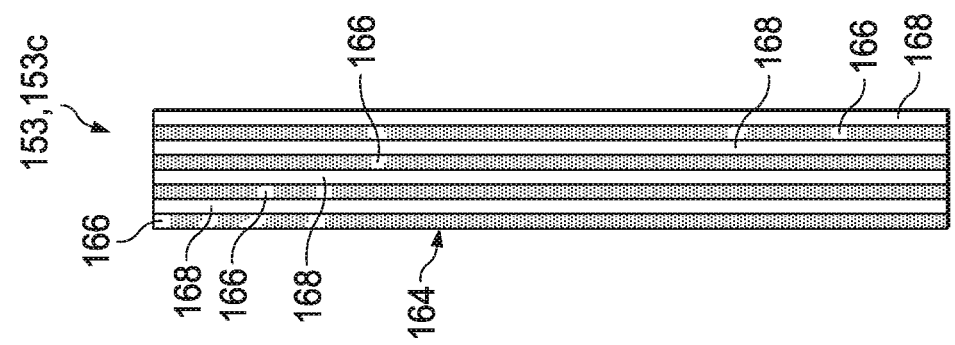
Figure 9B:
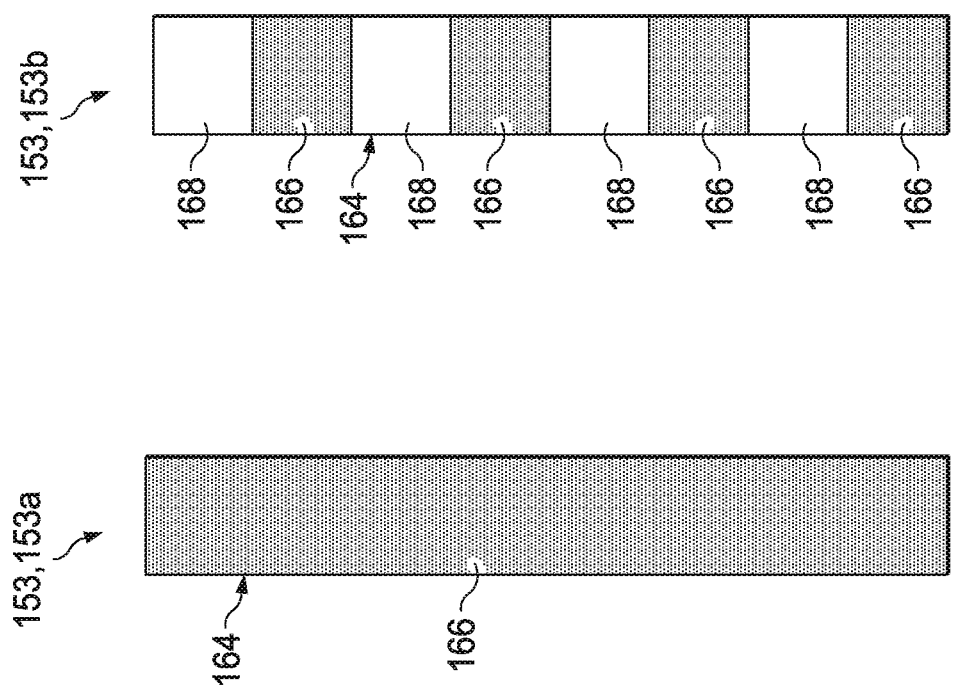
Figure 9A:
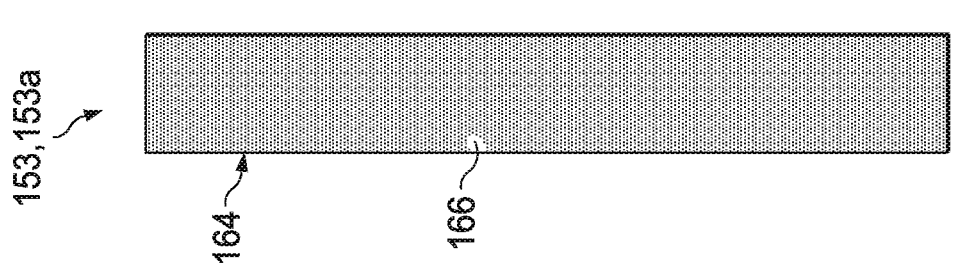

FIGS. 9A-9D illustrate additional example configurations for the polymeric enhancement layer 153. Referring to FIG. 9A, in some examples, the polymeric enhancement layer 153 may be a polymeric enhancement layer 153*a*. The polymeric enhancement layer 153*a* may include the silicone material 166 formed into the strip 164. Referring to FIG. 9B, in some examples, the polymeric enhancement layer 153 may be a polymeric enhancement layer 153*b*. The polymeric enhancement layer 153*b* may include alternating horizontal rows of the silicone material 166 and the acrylic material 168 formed into the strip 164. Referring to FIG. 9C, in some examples, the polymeric enhancement layer 153 may be a polymeric enhancement layer 153*c*. The polymeric enhancement layer 153*c* may include alternating vertical rows of the silicone material 166 and the acrylic material 168 formed into the strip 164. Referring to FIG. 9D, in some examples, the polymeric enhancement layer 153 may be a polymeric enhancement layer 153*d*. The polymeric enhancement layer 153*d* may include an alternating zig-zag pattern of the silicone material 166 and the acrylic material 168 formed into the strip 164.

In operation, in some example embodiments, a method for treating a tissue site may include disposing a dressing assembly according to this disclosure proximate to a tissue site. As described herein, the dressing assembly may include a dressing bolster, a comfort layer coupled to the dressing bolster, and a polymeric enhancement layer coupled to the comfort layer. Further, the method may include covering the dressing assembly with a sealing member to form a sealed space between the dressing assembly and the tissue site. Further, the method may include extracting fluid from the tissue site into the dressing assembly. Further, the method may include exposing the tissue site to the silicone material 166 or the acrylic material 168 or both the silicone material 166 and the acrylic material 168 associated with the various embodiments of the polymeric enhancement layer 153 described herein.

Figure 10:
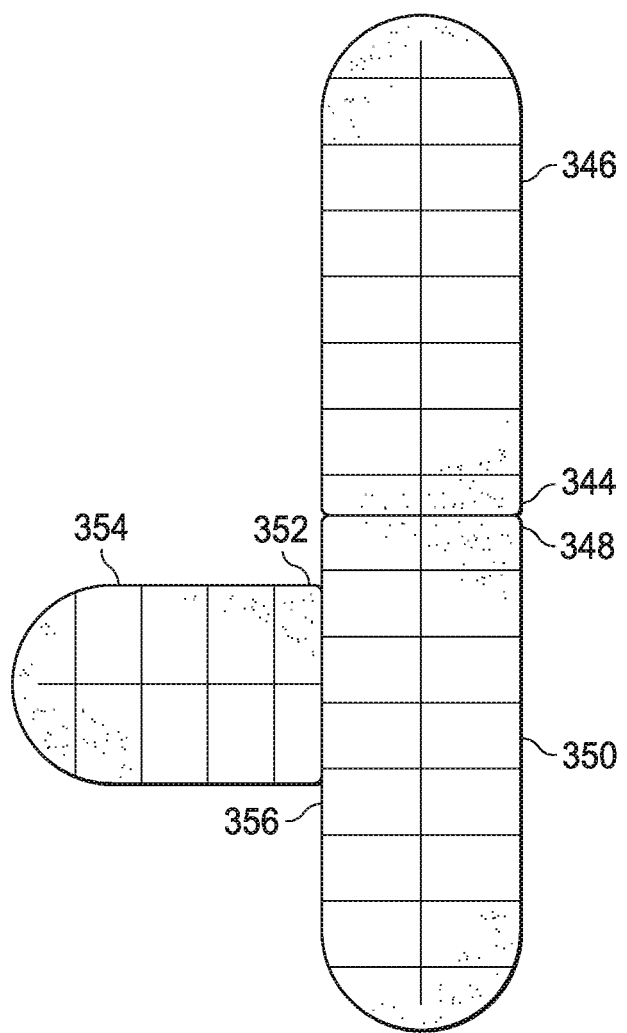
FIG. 10 is a plan view of a portion of an illustrative example embodiment of a treatment system for treating a tissue site.

Referring now to FIG. 10, the dressing assembly 314 may be cut to accommodate different sizes of linear wounds 306 prior to being disposed on the linear wound 306 and covered with the sealing member 340. For lengthy linear wounds 306, or multiple linear wounds 306 in a vicinity, more than one dressing assembly 314 may be used. A first longitudinal end 344 of a first dressing assembly 346 may be cut to have a flat surface. A first longitudinal end 348 of a second dressing assembly 350 may be cut or otherwise formed with a flat surface. The first longitudinal end 344 of the first dressing assembly 346 may be placed proximate to and abutting the first longitudinal end 348 of the second dressing assembly 350. The sealing rings (not shown but analogous to sealing ring 334) below the first dressing assembly 346 and the second dressing assembly 350 may coalesce or combine to form an integral sealing ring or gasket member.

A first longitudinal end 352 of a third dressing assembly 354 may be placed proximate to and abutting a lateral end or edge 356 of the second dressing assembly 350. Once the combination of dressing assemblies is arranged, the dressing assemblies 346, 350, 354 may be covered with a sealing member (not shown but analogous to sealing member 340 in FIG. 6C) to form a sealed space that contains the dressing assemblies 346, 350, 354. Reduced pressure may be then be applied to the sealed space to treat the linear wound or wounds.

Figure 11:
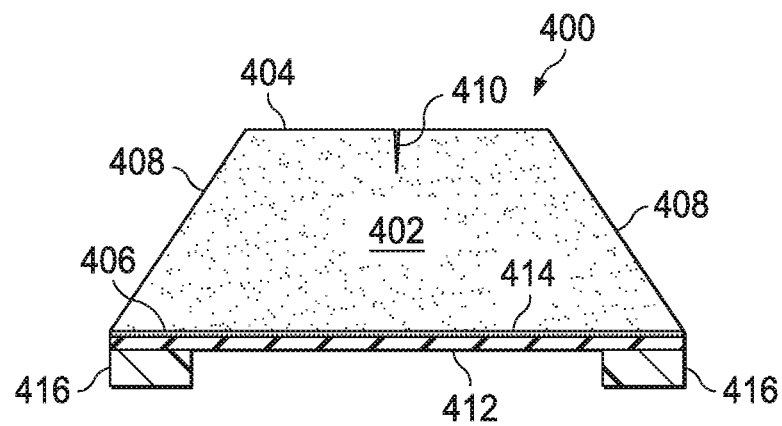
FIG. 11 is a cross-section of another illustrative example embodiment of a dressing assembly.

Referring now primarily to FIG. 11, depicted is a cross-section of an illustrative embodiment of a dressing assembly 400. The dressing assembly 400 may be used with treatment systems as described above, such as the treatment system 200. The dressing assembly 400 may include a dressing bolster 402. The dressing bolster 402 has a first side 404, a second, inward-facing side 406, and lateral edges 408. As with the previously presented dressing assemblies, the lateral edges 408 may take any shape, but are shown formed with approximately a 45 degree angle with respect to the second, inward-facing side 406. In the cross-section, a longitudinal notch 410 is visible. In addition, lateral notches (not shown) may be included on the first side 404, and notches (not shown) may be added to the lateral edges 408. The longitudinal notch 410 and any other notches help provide flexibility to the dressing assembly 400.

A comfort layer 412 may be coupled by an attachment device 414 to the second, inward-facing side 406 of the dressing bolster 402. A sealing ring 416 may be coupled to the comfort layer 412. The sealing ring 416 may be formed from the sealing materials previously mentioned. The sealing ring 416 may be coupled directly to the comfort layer 412, or may be attached to the comfort layer 412 by an attachment device, such as an acrylic adhesive (not shown).

Analogous to the previously described embodiments, in operation, the dressing assembly 400 may be placed over and about a linear wound and then covered with a sealing member to form a sealed space. Reduced pressure may then be delivered to the sealed space to treat the linear wound.

Figure 12:
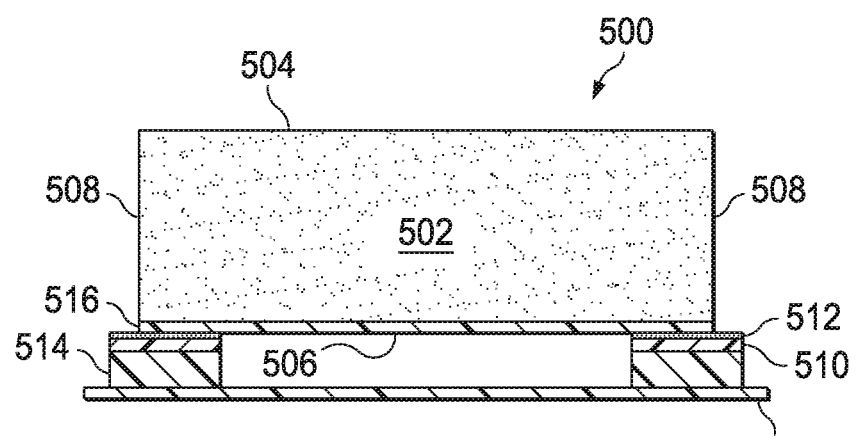
FIG. 12 is a cross-section of yet another illustrative example embodiment of a dressing assembly.

Referring now primarily to FIG. 12, depicted is a cross-section of another embodiment of a dressing assembly 500. The dressing assembly 500 may be analogous to the dressing assembly 400 of FIG. 11. The dressing assembly 500 includes a dressing bolster 502 having a first side 504 and a second, inward-facing side 506. The lateral edges 508 are substantially orthogonal to the second, inward-facing side 506. However, analogous to the dressing bolster 402 of FIG. 11, the lateral edges 508 of the dressing bolster 502 may have any angle or shape. In this embodiment, a sealing ring 514 may be laminated or coupled to a drape ring 510. The drape ring 510 may assist with positioning and manipulating the sealing ring 514 during assembly. The drape ring 510 may be coupled by an attachment device 512 to the second, inward-facing side 506 of the dressing bolster 502, or to an inward-facing side of a comfort layer 516. The sealing ring 514 may be covered by a release liner 518 prior to use.

In another embodiment (not explicitly shown), an attachment device, such as an adhesive, may be applied to the second, inward-facing side of a sealing ring to provide tackiness or enhanced tackiness between the sealing ring and an epidermis of a patient. The attachment device may be particularly beneficial when the sealing ring comprises a harder hydrocolloid than those previously mentioned, or when applied in cold conditions to provide time for the sealing material to warm up and become adequately tacky.

The appended claims set forth novel and inventive aspects of the subject matter in this disclosure. While shown in several illustrative embodiments, a person having ordinary skill in the art will recognize that the systems, apparatuses, and methods described herein are susceptible to various changes and modifications. Features may be emphasized in some example embodiments while being omitted in others, but a person of skill in the art will appreciate that features described in the context of one example embodiment may be readily applicable to other example embodiments. Further, certain features, elements, or aspects may be omitted from this disclosure if not necessary to distinguish the novel and inventive features from what is already known to a person having ordinary skill in the art. Features, elements, and aspects described herein may also be combined or replaced by different or alternative features serving the same, equivalent, or similar purpose without departing from the scope of the invention defined by the appended claims. Moreover, descriptions of various alternatives using terms such as "or" do not require mutual exclusivity unless clearly required by the context, and the indefinite articles "a" or "an" do not limit the subject to a single instance unless clearly required by the context. Further, the benefits and advantages described herein may relate to one embodiment or several embodiments. Even further, the steps of the methods described herein may be carried out in any suitable order, or simultaneously, where appropriate.

We claim:

1. A system for treating a tissue site, comprising:
a dressing assembly, comprising:
a dressing bolster having a first side and an opposing second side,
a comfort layer having a first side and an opposing second side, the first side of the comfort layer positioned on the second side of the dressing bolster,
a sealing ring positioned on the second side of the dressing bolster and around a circumference of the dressing bolster,
a sealing member covering the first side of the dressing bolster, and
a polymeric layer comprising silicone and having a first side and an opposing second side, wherein the first side of the polymeric layer is coupled to the second side of the comfort layer, wherein the second side of the polymeric layer is configured to directly contact the tissue site, wherein the polymeric layer comprises a plurality of apertures disposed through the polymeric layer between the first side and the second side of the polymeric layer, wherein the plurality of apertures through the polymeric layer are substantially aligned along a longitudinal axis of the dressing assembly and configured to be positioned along a length of an incision at the tissue site, wherein at least a portion of the second side of the comfort layer is exposed between the polymeric layer and the sealing ring, and wherein the second side of the comfort layer has a first area and the second side of the polymeric layer has a second area, and wherein the first area is larger than the second area; and
wherein the dressing assembly is configured to be coupled to a reduced-pressure source.

2. The system of claim 1, wherein the second area is less than 30 percent of the first area.

3. The system of claim 1, wherein at least a portion of the first area of the comfort layer and the second area of the polymeric layer are both configured to directly contact the tissue site.

4. The system of claim 1, wherein at least the portion of the comfort layer that is exposed extends around a periphery of the polymeric layer and is configured to be positioned directly against the tissue site.

5. The system of claim 1, wherein the portion of the comfort layer that is exposed surrounds a periphery of the polymeric layer such that both of the comfort layer and the polymeric layer are configured to directly contact the tissue site.

6. The system of claim 1, wherein the second side of the polymeric layer comprises an exposed pattern of silicone adhesive and acrylic adhesive configured to directly contact the tissue site.

7. The system of claim 1, wherein the polymeric layer comprises at least one strip of material substantially aligned along the longitudinal axis of the dressing assembly, and wherein the at least one strip of material comprises a silicone material or an acrylic material or both an acrylic material and a silicone material.

8. The system of claim 1, wherein the polymeric layer comprises:
   a film layer having a first side and an opposing second side;
   an acrylic layer positioned on the first side of the film layer and configured to be coupled to the second side of the comfort layer; and
   a silicone layer positioned on the second side of the film layer and configured to be positioned in direct contact with the tissue site.

9. The system of claim 8, wherein the acrylic layer forms at least a portion of the first side of the polymeric layer and the silicone layer forms at least a portion of the second side of the polymeric layer, and wherein the plurality of apertures are disposed through the film layer, the acrylic layer, and the silicone layer from the first side to the second side of the polymeric layer.

10. The system of claim 9, wherein the plurality of apertures are configured to be in fluid communication between the second side of the comfort layer and the tissue site.

11. The system of claim 9, wherein a portion of the acrylic layer on the first side of the polymeric layer is exposed on the second side of the polymeric layer through at least one of the plurality of apertures and configured to be in direct contact with the tissue site.

12. The system of claim 1, wherein the polymeric layer comprises:
   a silicone layer including the plurality of apertures disposed through the silicone layer; and
   an acrylic layer positioned between the second side of the comfort layer and the silicone layer, wherein at least a portion of the acrylic layer is exposed through the apertures in the silicone layer such that at least of portion of both the acrylic layer and the silicone layer form the second side of the polymeric layer that is configured to be in direct contact with the tissue site.

13. A system for treating a tissue site, comprising:
   a dressing assembly, comprising:
      a dressing bolster having a first side and a second side,
      a comfort layer having a first side and a second side, the first side of the comfort layer coupled to the second side of the dressing bolster,
      a gasket member positioned on the second side of the dressing bolster and around a circumference of the dressing bolster, and
      a polymeric enhancement layer having a first side and an opposing second side, wherein the first side of the polymeric enhancement layer is coupled to the second side of the comfort layer, wherein at least a portion of the second side of the comfort layer is exposed between the polymeric enhancement layer and the gasket member, wherein the second side of the polymeric enhancement layer and the portion of the second side of the comfort layer that is exposed are configured to directly contact the tissue site, and wherein at least the portion of the comfort layer that is exposed extends around a periphery of the polymeric enhancement layer and is configured to be positioned directly against the tissue site;
   a sealing member configured to cover the dressing assembly and to create a sealed space between the dressing assembly and the tissue site; and
   a reduced-pressure source configured to be coupled in fluid communication with the sealed space.

14. The system of claim 13, wherein the second side of the polymeric enhancement layer comprises an exposed pattern of silicone adhesive and acrylic adhesive configured to directly contact the tissue site.

15. The system of claim 14, wherein the exposed pattern includes one or more configurations selected from a group consisting of: dots of silicone adhesive, dots of acrylic adhesive, alternating vertical rows of silicone adhesive and acrylic adhesive, alternating horizontal rows of silicone adhesive and acrylic adhesive, and an alternating zig-zag pattern of silicone adhesive and acrylic adhesive.

16. The system of claim 13, wherein a portion of the comfort layer surrounds the periphery of the polymeric enhancement layer.

17. A dressing assembly, comprising:
   a dressing bolster comprising foam and having a first side and a second side;
   a comfort layer having a first side and a second side, the first side of the comfort layer coupled to the second side of the dressing bolster;
   a gasket member positioned on the second side of the dressing bolster and around a circumference of the dressing bolster; and
   a polymeric enhancement layer having a first side and an opposing second side, wherein the first side of the polymeric enhancement layer is coupled to the second side of the comfort layer, wherein at least a portion of the second side of the comfort layer is exposed between the polymeric enhancement layer and the gasket member, wherein the second side of the polymeric enhancement layer and the portion of the second side of the comfort layer that is exposed are configured to directly contact the tissue site, and wherein at least the portion of the comfort layer that is exposed extends around a periphery of the polymeric enhancement layer and is configured to be positioned directly against the tissue site.

18. The dressing assembly of claim 17, wherein the polymeric enhancement layer comprises:
   a film layer having a first side and an opposing second side;
   an acrylic layer positioned on the first side of the film layer and configured to be coupled to the second side of the comfort layer; and
   a silicone layer positioned on the second side of the film layer and configured to be positioned in direct contact with the tissue site.

19. The dressing assembly of claim 18, wherein the acrylic layer forms at least a portion of the first side of the polymeric enhancement layer and the silicone layer forms at least a portion of the second side of the polymeric enhancement layer, and wherein the polymeric enhancement layer further comprises a plurality of apertures disposed through the film layer, the acrylic layer, and the silicone layer from the first side to the second side of the polymeric enhancement layer.

20. The dressing assembly of claim 19, wherein the plurality of apertures are configured to be in fluid communication between the second side of the comfort layer and the tissue site.

21. The dressing assembly of claim 19, wherein a portion of the acrylic layer on the first side of the polymeric enhancement layer is exposed on the second side of the polymeric enhancement layer through at least one of the plurality of apertures and configured to be in direct contact with the tissue site.

22. The dressing assembly of claim 17, wherein the polymeric enhancement layer comprises:
   a silicone layer including a plurality of apertures disposed through the silicone layer; and
   an acrylic layer positioned between the second side of the comfort layer and the silicone layer, wherein at least a portion of the acrylic layer is exposed through the apertures in the silicone layer such that at least of portion of both the acrylic layer and the silicone layer form the second side of the polymeric enhancement layer that is configured to be in direct contact with the tissue site.

23. A method for treating a tissue site, comprising:
disposing a dressing assembly proximate to the tissue site, the dressing assembly comprising:
   a dressing bolster,
   a comfort layer coupled to the dressing bolster, and
   a polymeric enhancement layer coupled to the comfort layer;
positioning the polymeric enhancement layer along and in direct contact with an incision at the tissue site, wherein at least a portion of the comfort layer is exposed and extends around a periphery of the polymeric enhancement layer to position the portion of the comfort layer directly against the tissue site;
covering the dressing assembly with a sealing member to form a sealed space between the dressing assembly and the tissue site;
extracting fluid from the tissue site into the dressing assembly; and
exposing the tissue site to a silicone material or an acrylic material or both a silicone material and an acrylic material associated with the polymeric enhancement layer.

* * * * *